US012680092B2

(12) United States Patent
Juntunen et al.

(10) Patent No.: US 12,680,092 B2
(45) **Date of Patent: *Jul. 14, 2026**

(54) FUNGAL CELLULASE VARIANTS WITH IMPROVED STABILITY

(71) Applicant: AB Enzymes Finland Oy, Rajamäki (FI)

(72) Inventors: Kari Juntunen, Rajamäki (FI); Leena Valtakari, Rajamäki (FI); Susanna Mäkinen, Rajamäki (FI); Marika Alapuranen, Rajamäki (FI); Hendrik Hellmuth, Darmstadt (DE); Maike Anders, Idar-Oberstein (DE); Marc Mennicken, Aachen (DE); Ulrich Schwaneberg, Aachen (DE); David Schönauer, Aachen (DE); Pentti Ojapalo, Rajamäki (FI); Terhi Puranen, Rajamäki (FI)

(73) Assignee: AB Enzymes Finland Oy (FI)

( * ) Notice: Subject to any disclaimer, the term of this patent is extended or adjusted under 35 U.S.C. 154(b) by 1024 days.

This patent is subject to a terminal disclaimer.

(21) Appl. No.: 17/291,424

(22) PCT Filed: Nov. 12, 2019

(86) PCT No.: PCT/FI2019/050804
§ 371 (c)(1),
(2) Date: May 5, 2021

(87) PCT Pub. No.: WO2020/099719
PCT Pub. Date: May 22, 2020

(65) Prior Publication Data
US 2022/0002697 A1 Jan. 6, 2022

(30) Foreign Application Priority Data
Nov. 13, 2018 (EP) .................................... 18205848

(51) Int. Cl.
| | |
|---|---|
| *C12N 9/42* | (2006.01) |
| *C11D 3/386* | (2006.01) |
| *C12N 1/20* | (2026.01) |
| *C12N 15/70* | (2006.01) |
| *D06M 16/00* | (2006.01) |
| *D06M 101/06* | (2006.01) |

(52) U.S. Cl.
CPC ........ *C12N 9/2437* (2013.01); *C11D 3/38645* (2013.01); *C12N 1/20* (2013.01); *C12N 15/70* (2013.01); *C12Y 302/01004* (2013.01); *D06M 16/003* (2013.01); *D06M 2101/06* (2013.01); *D06M 2200/25* (2013.01)

(58) Field of Classification Search
CPC .............. C12N 9/2437; C11D 3/38645; C12Y 302/01004; D06M 16/003; D06M 2101/06; D06M 16/00
See application file for complete search history.

(56) References Cited

U.S. PATENT DOCUMENTS 9,279,163 B2 * 3/2016 Montalibet .......... C12N 9/2437
2009/0162916 A1 6/2009 Adney et al.

FOREIGN PATENT DOCUMENTS

| CN | 101171333 A | 4/2008 |
|---|---|---|
| CN | 101346464 A | 1/2009 |
| EP | 1123974 A1 | 8/2001 |
| WO | 2007071820 A1 | 6/2007 |
| WO | 2016066896 A1 | 5/2016 |
| WO | 2017106676 A1 | 6/2017 |

OTHER PUBLICATIONS

Livingstone, et al., "Protein Sequence Alignments: a strategy for the hierarchical analysis of residue conservation", CABIOS, vol. 9, No. 6, 1993, 745-756 (Year: 1993).*
Camps, et al., "Genetic Constraints on Protein Evolution", Crit Rev Biochem Mol Biol., 42(5), 2007 (Year: 2007).*
ABSS Sequence Alignment. SEQ ID 1 U.S. Appl. No. 17/291,424 vs SEQ ID 1 U.S. Appl. No. 17/291,125 (Year: 2018).*
ABSS Sequence Alignment. SEQ ID 1 U.S. Appl. No. 17/291,424 vs SEQ ID 4 U.S. Appl. No. 17/291,125 (Year: 2018).*
ABSS Sequence Alignment. SEQ ID 1 U.S. Appl. No. 17/291,424 vs SEQ ID 12 U.S. Appl. No. 15/522,386 (Year: 2017).*
ABSS Sequence Alignment. SEQ ID No. 1 U.S. Appl. No. 17/291,424 vs SEQ ID No. 1 U.S. Appl. No. 15/522,386 (Year: 2017).*
GenBank AOL86446.1 Sequence 146 from U.S. Pat. No. 9,279,163 (Year: 2016).*
ABSS Sequence Alignment. SEQ_ID 1 U.S. Appl. No. 17/291,424 vs SEQ ID 111 US20090162916A1 (Year: 2009).*
ABSS Sequence Alignment. SEQ ID 1 U.S. Appl. No. 17/291,424 vs SEQ ID 146 U.S. Pat. No. 9,279,163 (Year: 2016).*
Reetz, M.T. (2011), Laboratory Evolution of Stereoselective Enzymes: A Prolific Source of Catalysts for Asymmetric Reactions. Angew. Chem. Int. Ed., 50: 138-174. (Year: 2011).*
Druzhinina, et al. Genetic engineering of Trichoderma reesei cellulases and their production. Microb Biotechnol. Nov. 2017; 10(6): 1485-1499. doi: 10.1111/1751-7915.12726. Epub May 29, 2017. PMID: 28557371; PMCID: PMC5658622. (Year: 2017).*
Escuder-Rodri-guez, et al. Cellulases from Thermophiles Found by Metagenomics. Microorganisms. Jul. 10, 2018;6(3):66. doi: 10.3390/microorganisms6030066. PMID: 29996513; PMCID: PMC6165527. (Year: 2018).*

(Continued)

*Primary Examiner* — Melenie L Gordon
*Assistant Examiner* — Dennis Ignatius Armato, Jr.
(74) *Attorney, Agent, or Firm* — Elmore Patent Law Group, P.C.; Joseph C. Zucchero; Carolyn S. Elmore

(57) ABSTRACT

The invention relates to novel variants of fungal endoglucanases. The invention further relates to enzyme preparations and detergent compositions comprising the variant as well as to processes for treating cellulosic material with the variant. The variants have depilling, antipilling and/or anti-greying performance, and improved stability in the presence of proteases.

29 Claims, 7 Drawing Sheets
Specification includes a Sequence Listing.

(56)                    References Cited

OTHER PUBLICATIONS

Godoy, et al. Structure, computational and biochemical analysis of PcCel45A endoglucanase from Phanerochaete chrysosporium and catalytic mechanisms of GH45 subfamily C members. Sci Rep 8, 3678 (2018). https://doi.org/10.1038/s41598-018-21798-9 (Year: 2018).*

Bailey, M. et al., "Induction, isolation and testing of stable Trichoderma reesei mutants with improved production of solubilizing cellulase", Enzyme Microb. Technol., 3, 1981, 153-157.

Gellissen, G. "Production of recombinant proteins. Novel microbial and eukaryotic expression systems", Gellissen G. (ed.). Wiley-VCH Verlag Gmbh & Co. Wein-heim, Germany, 2005.

Haakana, H. et al., "Cloning of cellulase genes from Melanocarpus albomyces and their efficient expression in Trichoderma reesei", Enzyme Microb. Technol., 34, 2004, 159-167.

Henrissat, B. et al., "A classification of glycosyl hydrolases based on amino acid sequence similarities", Biochem. J., 280, 1991, 309-316.

Henrissat, B. et al., "New families in the classification of glycosyl hydrolases based on amino acid sequence similarities", Biochem. J., 293, 1993, 781-788.

Henrissat, B. et al., "Updating the sequence-based classification of glycosyl hydrolases", Biochem. J., 316, 1996, 695-696.

Joutsjoki, V. V. et al., "Transformation of Trichoderma reesei with the Hormoconis resinae glucoamylase P (gamP) gene: production of a heterologous glucoamylase by Trichoderma reesei", Curr. Genet. 24, 1993, 223-228.

Karhunen, T. A. et al., "High frequency one-step gene replacement in Trichoderma reesei. I. Endoglucanase I overproduction", Mol. Gen. Genet., 241, 1993, 515-522.

Paloheimo, M. et al., "High-yield production of a bacterial xylanase in the filamentous fungus Trichoderma reesei requires a carrier polypeptide with an intact domain structure", Appl. Env. Microbiol., 69, 2003, 7073-7082.

Penttila, M. et al., "A versatile transformation system for the cellulolytic filamentous fungus Trichoderma reesei", Gene, 61, 1987, 155-164.

Sambrook, J. et al., "Molecular cloning, a laboratory manual", 3rd Edition; vol. 1, Cold Spring Harbor Laboratory, New York, US., 2001.

Zhou, Q. et al., "Characterization of a novel thermostable GH45 endoglucanase from Chaetomium thermophilum and its biodegradation of pectin", J. Boisci. and Bioeng., vol. 124, No. 3, 2017, 271-276.

* cited by examiner

FUNGAL CELLULASE VARIANTS WITH IMPROVED STABILITY

FIELD OF THE INVENTION

The invention relates to novel variants of cellulases. The invention further relates to enzyme compositions and detergents comprising at least one of the novel variants of cellulases as well as to processes for treating cellulosic material with said variants. The novel variants of cellulases are especially useful in textile treatment and detergent applications.

SEQUENCE LISTING

The sequence listing submitted via EFS, in compliance with 37 CFR § 1.821(c)(1), is incorporated herein by reference. The sequence listing ASCII text file submitted via EFS contains the file "60253004USSequenceST25.txt", created on Apr. 16, 2021, which is 6,769 bytes in size.

BACKGROUND OF THE INVENTION

Cellulolytic enzymes or cellulases are enzymes having cellulolytic activity, which means that they are capable of hydrolysing cellulosic substrates or derivatives thereof into smaller saccharides. Cellulolytic enzymes thus include both cellulases and hemicellulases. Cellulases include (1) endo-glucanases (EG, EC 3.2.1.4) which cut internal beta-1,4-glucosidic bonds; (2) exoglucanases or cellobiohydrolases (CBH, EC 3.2.1.176, EC 3.2.1.91) that cut the dissaccharide cellobiose from the reducing or non-reducing end of the crystalline cellulose polymer chain and (3) beta-1,4-glucosi-dases (BG, EC 3.2.1.21) which hydrolyze the cellobiose and other short cello-oligosaccharides to glucose. Cellulases can contain a cellulose binding module (CBM) that are separated from the catalytic domain by a flexible spacer known as a linker or linker peptide.

Cellulases are utilized, based on their properties, in various industrial fields. In the textile industry, cellulases are used, for example, in denim finishing for creating a fashionable stone washed appearance in denim cloths in a biostoning process, and they are also used, for instance, to clean fuzz and prevent formation of pills on the surface of cotton garments. In detergent industry, cellulases are used to brighten colors, to prevent graying and pilling of garments and to improve cleaning. Cellulases are further used in food industry, including baking, and animal feed manufacturing, and they have a great potential in the pulp and paper industry, for instance, in deinking to release ink from fiber surfaces, in improving pulp drainage and fiber modification, in dissolving pulp, in energy reduction, in refining and drying stages of paper, board and pulp production. Cellulases are also utilized in hydrolysis of lignocellulosic material for, e.g. bioethanol production.

Although industrially well-performing cellulases and their variants are described in, e.g., WO2016/066896 and WO2017/106676, a need still exists for new cellulolytic enzymes with altered properties, such as improved stability and improved performance, in varying industrial applications.

SUMMARY OF THE INVENTION

An object of the present invention is to provide novel variants of fungal cellulases that show improved stability in detergent, when compared to the parental enzyme to which substitutions are made. The objects of the invention are achieved by the variants of a GH45 cellulase polypeptide characterized by what is stated in the independent claims. Preferred embodiments of the invention are disclosed in the dependent claims.

The invention discloses a number of amino acid residue positions in GH45 cellulases that are important for the stability and thereby for their performance. Thus, the set of positions as defined below can be used to improve properties of GH45 cellulases by manufacturing variants of GH45. The novel variants are shown in the examples to have improved stability compared to the parent cellulase ACM88 deriving from *Acremonium thermophilum* Cel45A cellulase.

The results obtained for the variants of ACM88 can be applied to manufacture variants of other GH45 cellulases, because of the conserved structure and function of the GH45 family. In particular, the novel variants have improved performance in color revival (pilling removal/depilling) and color maintenance/color care (antipilling) and they were shown to have excellent stability in the presence of a protease in several detergent compositions. Especially the variants show improved stability in protease containing detergents in long-term experiments at 30° C. temperatures.

According to the first aspect of the invention is disclosed a variant of a GH45 cellulase polypeptide, or an active fragment thereof, comprising substitutions in the positions 167, 210, 215, 220 and 225, wherein the amino acid positions are numbered with reference to the amino acid sequence set forth in SEQ ID NO: 1. According to the second aspect of the invention is provided an isolated nucleic acid molecule comprising a nucleotide sequence, which encodes the variant of the first aspect.

According to the third aspect of the invention is provided a recombinant expression vector comprising a nucleotide sequence encoding the variant of the first aspect operably linked to regulatory sequences capable of directing expression of the gene encoding said variant cellulase in a suitable host.

According to the fourth aspect of the invention is provided a host cell comprising the recombinant expression vector according to the third aspect.

According to the fifth aspect of the invention is provided a method of producing the variant of the first aspect, said method comprising the steps of culturing the host cell of the fourth aspect and optionally recovering the variant.

According to the sixth aspect of the invention is provided an enzyme composition comprising the variant of the first aspect.

According to the seventh aspect of the invention is provided a detergent composition comprising the variant of the first aspect or the enzyme composition of the sixth aspect.

According to the eighth aspect of the invention is provided a method for treating cellulosic material, wherein the method comprises reacting the cellulosic material with the variant of the first aspect or the enzyme composition of the sixth aspect.

According to the ninth aspect of the invention is provided a use of the variant of the first aspect or the enzyme composition of the sixth aspect in detergents, in treating fiber, in wood-derived pulp, in biomass hydrolysis, in textile application, in food or feed application, or in any application involving modification, degradation or removal of cellulose containing material.

According to another aspect of the invention is provided a method for antigreying, stain removal, fiber and color care, biostoning or biofinishing which comprises a step of adding the variant of the first aspect, or the enzyme composition of the sixth aspect, to liquid used in treating fabric containing cellulose or cellulose derivative or garments or other textile materials like fabrics or garments or yarn.

According to another aspect is provided a variant of a GH45 cellulase polypeptide, or an active fragment thereof, comprising at least one substitution in the positions 167, 210, 215, 220 and 225, wherein the amino acid positions are numbered with reference to the amino acid sequence set forth in SEQ ID NO: 1. In an embodiment the variant comprises at least 2, 3, 4, or 5 substitutions selected from the above positions. As is seen from the examples where performance and stability of the variants were tested, each of these positions is useful in improving properties of the variant, and an even higher improvement is achieved when more positions are substituted in combination.

BRIEF DESCRIPTION OF THE DRAWINGS

In the following the invention will be described in greater detail by means of preferred embodiments with reference to the attached drawings, in which:

FIG. 2A shows the color revival performance of the variants D144-D148 compared to ACM88.

FIG. 2B shows the color revival (depilling) performance of the variants D149-D152 compared to ACM88.

FIG. 3 shows the residual performance as color revival (depilling) effect after storage in commercial liquid detergent containing of protease (0.7% Savinase 16 L) at room temperature (approx. 20-22° C.) for 4 days.

FIG. 4 shows the residual enzyme activity (NCU) after storage in commercial liquid detergent containing of protease (0.7% Savinase 16 L) at room temperature (approx. 20-22° C.) for 4 days.

SEQUENCE LISTING

Figure 1:
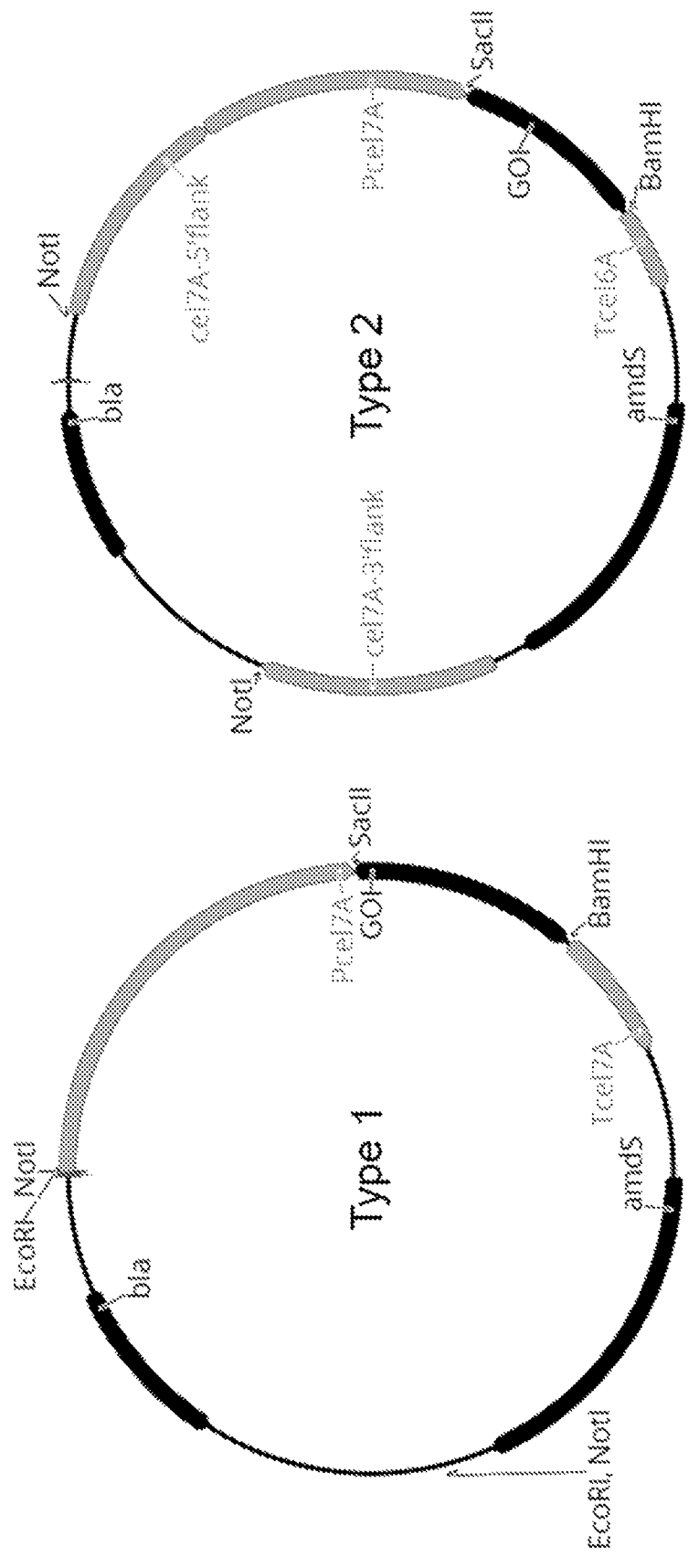
FIG. 1 shows a schematic picture of the expression plasmid types used in the transformation of *Trichoderma reesei* for expression of the gene of interest (GOI). The recombinant genes were under control of *T. reesei* cel7A promoter (Pcel7A) and transcription termination was ensured with the addition of the *T. reesei* cel7A (Tcel7A) in plasmid Type 1 or *T. reesei* cel6A (Tcel6A) terminator in plasmid Type 2. The amdS gene (amdS) was included for selection of the transformants. Ampicillin resistance gene (bla) was used in plasmid construction. Pictures were generated using Geneious version 11.0 created by Biomatters.

SEQ ID NO: 1 is the amino acid sequence of the mature ACM88 cellulase deriving from the *Acremonium thermophilum* GH45-cellulase including amino acids from Leu1 to Leu281.

SEQ ID NO: 2 is the full-length amino acid sequence of ACM88 cellulase deriving from the *Acremonium thermophilum* GH45-cellulase including amino acids from Met1 to Leu298.

SEQ ID NO: 3 is the nucleotide sequence of the full-length ACM88 cellulase deriving from *Acremonium thermophilum* ce145-cellulase.

DETAILED DESCRIPTION OF THE INVENTION

The present invention relates to cellulases and in particular to endoglucanases. Specifically, the present invention relates to fungal endoglucanases belonging to glycosyl hydrolase family 45 (GH45), especially to variants of these endoglucanases. In an embodiment of the invention variants of *Acremonium thermophilum* Cel45A endoglucanase polypeptide are disclosed.

"Glycosyl hydrolase family 45" refers to the glycosyl hydrolase family as defined by Henrissat 1991, and Henrissat and Bairoch 1993, 1996.

In an embodiment of the invention the variant has at least 80% sequence identity with a GH45 cellulase. In an embodiment the variant has at least 80% sequence identity with the catalytic core of the GH45 cellulase. Preferably the variant has at least 80% sequence identity with the amino acid sequence of SEQ ID NO: 1. In another embodiment the variant has at least 80%, 85%, 90%, 95% or 99% sequence identity with the residues 1-207 of the SEQ ID NO: 1. Said sequence identity is advantageous in case a structure or properties that very closely resemble those obtained in the examples below are desired from the variant. The skilled person is able to measure essential properties of a variant, such as production level, enzyme activity and enzyme stability by using the methods of the Examples below, and to select a variant, which has desired characteristics. The particular combination of the substitutions in the present variant of the first aspect is advantageous in obtaining a variant, which has improved performance and stability as shown in the examples below. However, when a polypeptide having a slightly different amino acid sequence than ACM88 (SEQ ID NO: 1) is used as a "template polypeptide" or a "parental polypeptide" to which the substitutions are made according to the present invention, said template polypeptide may not have exactly the same amino acid in the position corresponding to the positions Q167, N210, N215, N220 and N225 of SEQ ID NO: 1. In such a case the amino acid of the template polypeptide in the corresponding position shall be substituted, instead. Because the template polypeptide necessarily belongs to the same enzyme family and has a very similar amino acid sequence, it is much more likely than not that the substitution in the same position of the template polypeptide results into the same, or substantially the same or equivalent, effect as the same substitution in the ACM88 sequence. Thus, the technical effect is achieved for the present variants. In an embodiment of the invention the substitutions of the variant comprise the substitutions of Q167, N210, N215, N220 and N225. More preferably the substitutions comprise the substitutions Q167Y, N210S, N215R/S, N220S and N225S. Such a set of substitution is advantageous when manufacturing an ACM88 variant, or a variant of another GH45 family member, which has the same amino acids in said positions.

In an embodiment of the invention the substitutions comprise the substitutions 167Y, 210S, 215R, 220S and 225S. Such a set of substitution is advantageous when manufacturing a GH45 variant, which has different amino acids in said positions but for which similar characteristics as obtained in the examples below are desired.

These embodiments are advantageous to be able to provide variants from GH45 cellulases that have a very similar amino acid sequence with SEQ ID NO: 1 and have amino acids in said positions. The substitutions Q167Y, N210S, N215R/S, N220S and N225S are particularly advantageous, but the skilled person understands that other substitutions at said positions may also be useful to achieve a desired technical effect. The skilled person can use the assays provided in the Examples below to determine e.g. stability and performance of a variant.

In an embodiment of the invention the variant has an improved stability in comparison to the parental polypeptide.

In an embodiment the meaning of stability includes storage stability and stability during use, e.g. during a wash process (in wash stability) and reflects the stability of the variant cellulase according to the invention as a function of time, e.g. how much activity and/or wash performance is retained when the variant cellulase is kept in solution, in particular in a detergent solution in the presence of protease. The skilled person can use the assays provided in the Examples below to determine stability of a variant.

In an embodiment of the invention the variant further comprises one or more substitutions in the positions 23, 44, 65, 66, 77, 193, 219, 242 and 244, preferably one or more substitutions in the positions S23, K44, D65, N66, A77, T193, G219, S242 and G244.

Each of said positions is shown in the examples to improve stability and/or performance of the variant when combined with substitutions of the variant of the first aspect.

In an embodiment of the invention the further substitution is one or more of the substitutions S23P, K44N, D65E, N66Q, A77S, T193V, G219S, S242G and G244T.

In an embodiment of the invention the variant comprises the following substitutions: S23P, D65E, N66Q, A77S, Q167Y, N210S, N215R, G219S, N220S, N225S and G244T.

In an embodiment of the invention the host cell is preferably selected from the group consisting of:

fungal cells, filamentous fungal cells from Division Ascomycota, Subdivision Pezizomycotina; preferably from the group consisting of members of the Class Sordariomycetes, Subclass Hypocreomycetidae, Orders Hypocreales and Microascales and *Aspergillus, Chrysosporium, Myceliophthora* and *Humicola;*
more preferably from the group consisting of Families Hypocreacea, Nectriaceae, Clavicipitaceae, Microascaceae, and Genera *Trichoderma* (anamorph of *Hypo-*

*crea), Fusarium, Gibberella, Nectria, Stachybotrys, Claviceps, Metarhizium, Villosiclava, Ophiocordyceps, Cephalosporium,* and *Scedosporium;*
more preferably from the group consisting of *Trichoderma reesei (Hypocrea jecorina), T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. moniliformis, G. zeaea, Nectria (Haematonectria) haematococca, Stachybotrys chartarum, S. chlorohalonata, Claviceps purpurea, Metarhizium acridum, M. anisopliae, Villosiclava virens, Ophiocordyceps sinensis, Acremonium (Cephalosporium) chrysogenum,* and *Scedosporium apiospermum,* and *Aspergillus niger, Aspergillus awamori, Aspergillus oryzae, Chrysosporium lucknowense, Myceliophthora thermophila, Humicola insolens,* and *Humicola grisea,*
bacterial cells, preferably gram positive Bacilli such as *B. subtilis, B. licheniformis, B. megaterium, B. amyloliquefaciens, B. pumilus,* gram negative bacteria such as *Escherichia coli,* actinomycetales such as *Streptomyces* sp., and
yeasts, such as *Saccharomyces cerevisiae, Pichia pastoris, Yarrowia lipolytica,* most preferably *Trichoderma reesei* or *Bacillus.*

In a preferable embodiment of the invention the enzyme composition may comprise the variant of the invention and:

a. optionally at least one polyol selected from propylene glycol, glycerol, a sugar, sugar alcohol, sorbitol, hexylene glycol;
b. optionally at least one preservative selected preferably from organic acids, e.g. benzoic acid, citric acid, ascorbic acid, sorbic acid, and salts thereof, sodium benzoate, hydroxybenzoate, benzisothiazolinone (BIT), or a combination thereof;
c. optionally at least one inhibitor selected from formic acid, lactic acid, boric acid, boric acid derivative, aromatic borate ester, phenyl boronic acid derivative, peptide, other reversible subtilisin inhibitors, or a combination thereof;
d. optionally at least one enzyme selected from proteases, amylases, cellulases, lipases, xylanases, mannanases, cutinases, esterases, phytases, nucleases, pectinases, pectinolytic enzymes, pectate lyases, carbohydrases, arabinases, galactanases, xanthanases, xyloglucanase, laccases, peroxidases and oxidases with or without a mediator, or a combination thereof;
e. optionally at least one salt selected from sodium chloride, potassium chloride, potassium (hydrogen) phosphate, sodium (hydrogen)phosphate, ammonium sulfate, potassium sulfate, or a combination thereof; and
f. optionally at least one filler or carrier selected from maltodextrin, flour, sodium chloride, sulfate, sodium sulfate, sodium acid pyrophosphate, tetrasodium pyrophosphate, polyethylene glycol, or a combination thereof.

In an embodiment the enzyme composition is in the form of liquid composition or a solid composition such as solution, dispersion, paste, powder, pellet, granule, granulate, coated granulate, tablet, cake, crystal, crystal slurry or gel.

In an embodiment the detergent composition is in the form of liquid detergent or a solid detergent, preferably in the form of a bar, a homogenous tablet, a tablet having two or more layers, a pouch having one or more compartments, a regular or compact powder, a granule, a paste, a gel, or a regular, compact or concentrated liquid.

In an embodiment the detergent composition comprises one or more additional enzymes selected from the group of proteases, amylases, cellulases, lipases, xylanases, mannanases, cutinases, esterases, nucleases, pectinases, pectate lyases, pectinolytic enzymes, carbohydrases, arabinases, galactanases, xanthanases, xyloglucanases, laccases, peroxidases and oxidases, preferably from the group of proteases, amylases, cellulases and lipases, and wherein the detergent composition preferably comprises one or more of the surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, buffers, preservatives, sod suppressors, solvents, and structurants for liquid detergents, structure elasticizing agents, enzyme inhibitors or stabilizers, enzyme activators, transferase(s), hydrolytic enzymes, oxido reductases, bluing agents and fluorescent dyes, antioxidants, and solubilizers.

In an embodiment of the invention the cellulosic material to be treated is textile material, plant material used in animal feed, or wood-derived pulp, or secondary fiber.

In an embodiment of the invention the variant or the enzyme composition is for use in detergents, in treating fiber, in wood-derived pulp, in biomass hydrolysis, in textile applications, in food or feed application, or in any application involving modification, degradation or removal of cellulose containing material.

In an embodiment of the invention the method concerns use in textile industry or in treating cellulosic textile material, and it comprises contacting the textile material with the detergent composition. Instead of the detergent composition the enzyme composition can also be used.

In an embodiment of the invention the textile materials that are used in the present methods or uses are manufactured of natural cellulose containing fibers or manmade cellulose containing fibers or they are mixtures thereof.

In an embodiment is provided a variant comprising the substitutions as defined for each variant name in Table 3 below. Said variants are particularly advantageous because they can be produced in recombinant host cell and they show improved stability measured as color revival performance. In an embodiment the variant is a fungal endoglucanase, or derived from a fungal endoglucanase, preferably a fungal GH45 endoglucanase.

In a particular embodiment the present invention relates to a variant cellulase polypeptide, or an active fragment thereof, comprising an amino acid sequence encoded by the nucleotide sequence set forth in SEQ ID NO: 3 and at least the following substitutions: Q167Y, N210S, N215R/S, N220S and N225S, wherein the amino acid positions of the variant, or an active fragment thereof, are numbered with reference to the amino acid sequence set forth in SEQ ID NO: 1. In another embodiment the variant cellulase polypeptide comprises the following substitutions S23P, D65E, Q167Y, N210S, N215R, G219S, N220S, N225S and G244T.

In the present invention the cellulase variants are preferably derived from a parental molecule designated as ACM88 (WO2016/066896). ACM88 contains the Cel45A catalytic core deriving from *A. thermophilum* attached to a linker and CBM region deriving from *T. reesei* Cel7A (nucleic acid sequence SEQ ID NO: 3, corresponding to amino acid sequence SEQ ID NO: 2).

The term "derived from" covers the terms "originated from", "obtained from", "obtainable from", "isolated from" and "created from" and generally indicates that one specified material has its origin in another specified material or has features that can be described with reference to the other specified material.

A variant polypeptide has a "mutation" i.e. any change or alteration in an amino acid sequence that is different from the starting amino acid. As used herein, a "variant" is a polypeptide that is derived from a parent by substitution, deletion, addition or replacement of one or more amino acids. Preferably the variant polypeptide of the invention has a substitution. In some embodiments the variant polypeptide may have a deletion of one or more amino acid. In one embodiment the variant may be a combination of substitutions and deletions in the amino acid sequence of the polypeptide.

Substitutions are described using of the following nomenclature: amino acid residue in the protein scaffold; position; substituted amino acid residue(s).

According to this nomenclature the substitution of, for instance, a serine residue for a glycine residue at position 20 is indicated as Ser20Gly or S20G. The variants were designed by protein engineering techniques on the basis of amino acid sequence comparison and three-dimensional structure analysis. The variants were generated by mutagenesis i.e. by deliberately introducing changes in DNA to produce mutant gene products i.e. proteins. The changes or modifications of the parental nucleotide sequence may be introduced by several methods including e.g. site-directed and random mutagenesis. For site-directed mutagenesis a protein structure and good understanding of the structure-function relationship is beneficial. In the absence of such deep understanding, methods based on random mutagenesis may be used.

Stability of the variant may be improved by a substitution of at least one amino acid with cysteine residue or insertion of one or more cysteine residues which creates at least one disulfide bridge. A stable variant may also be obtained e.g. by altering hydrogen bond contacts, altering charge distribution, introduction of a salt bridge, introduction of metal binding sites, filling an internal structural cavity with one or more amino acids with bulkier side groups (in e.g. regions which are structurally mobile), substitution of histidine residues with other amino acids, removal of a deamination site, or by helix capping.

The variants of the invention are preferably recombinantly produced fusion proteins. They are conveniently prepared using the generally known recombinant DNA technology. Briefly, the polynucleotide encoding the variant cellulase is cloned and inserted into an expression vector, transformed into a host cell and expressed. Methods for protein production by recombinant technology in different host systems are well known in the art (Sambrook and Russell, 2001; Gellissen, 2005). Preferably, the variant polypeptides are produced as extracellular proteins that are secreted into the culture medium, from which they can easily be recovered and isolated.

The variants may comprise in addition to the "catalytic core" domain, which forms the active or functional site of the enzyme, one or more "cellulose binding domains" ("CBDs"), also named as carbohydrate binding domains/modules (CBD/CBM) located either at the N- or C-terminus of the catalytic domain. CBMs have carbohydrate-binding activity and they mediate the binding of cellulase to crystalline cellulose but have little or no effect on hydrolytic activity of the enzyme on soluble substrates.

The variants of the invention may also contain a signal sequence and/or a linker connecting the CBM and catalytic domain via a flexible and often highly glycosylated region. By a "linker" or "spacer" as used herein is meant a flexible polypeptide comprising at least two amino acids that is linking two molecules of interest together. For example, a fusion protein of an enzyme core with a CBM is provided by fusing a DNA sequence encoding the enzyme core, a DNA sequence encoding the linker and a DNA sequence encoding the CBM sequentially into one open reading frame and expressing this construct. The CBM and the linker region may be heterologous or homologous. "Heterologous" as used in the present context means that the CBM and/or the possible linker part of the variant endoglucanase polypeptide are obtained from a different organism than the cellulolytically active core domain. "Homologous" as used herein means that the CBM and/or the possible linker part of the variant are from the same organism as the cellulolytically active core.

"An enzymatically active fragment" or an "active fragment" refers to a part of the amino acid sequence that is long enough to have the desired enzymatic activity and improved stability in the presence of detergent and/or protease when compared to parent polypeptide. In other words, an enzymatically active fragment may be e.g. only the mature part of the polypeptide or even a subsequence of the mature part. It may or may not contain a linker and a CBM domain. The enzymatic activity refers herein to cellulolytic activity meaning catalytic ability of the variant cellulase polypeptide or its fragment to hydrolyse cellulose or derivatives thereof. The enzymatic activity may be determined as described in Example 1.

As used herein, "sequence identity" means the percentage of exact matches of amino acid residues between two aligned sequences over the number of positions where there are residues present in both sequences. When one sequence has a residue with no corresponding residue in the other sequence, a gap is allowed in the alignment. That position is not counted in the denominator of the identity calculation in the alignment program. Identity is a value determined with the Pairwise Sequence Alignment tool EMBOSS Needle at the EMBL-EBI website (www.ebi.ac.uk/Tools/psa/emboss_ needle/) with the following parameters: BLOSUM62, Gap open 10, Gap extend 0.5.

The present invention relates further to novel polynucleotides which comprise nucleotide sequences encoding the enzymatically active variant cellulase of the invention, including complementary strands thereof. The polynucleotides of the invention are recombinant molecules containing genetically engineered non-naturally occurring sequences. "Polynucleotide" as used herein refers to both RNA and DNA, and it may be single stranded or double stranded. It may also be complementary DNA (cDNA). With cDNA is meant a DNA molecule synthesized from a messenger RNA template obtained from a eukaryotic or prokaryotic organism. Further, the polynucleotide may be degenerate as a result of the genetic code to any one of the sequences as defined above. This means that different codons may code for the same amino acid.

The present invention relates to a recombinant expression "vector" comprising a polynucleotide encoding the variant as characterized above, operably linked to regulatory sequences, which are capable of directing the expression of a gene encoding said variants in a suitable host. Said regulatory sequences may originate from the host organism, from another organism or can be synthetic. The expression vector may further comprise marker genes for selection of the transformant strains or the selection marker may be introduced to the host in another vector construct by co-transformation.

Still the present invention relates to a production "host cell", which can be any organism capable of expressing the desired polypeptide. The host cell may be heterologous or homologous. The host cell may or may not be genetically modified. Preferably a recombinant host cell is used which is modified to express and secrete the variant of the invention as its main activity or one of its main activities. This can be done by deleting genes encoding major endogenous secreted enzymes e.g. the four major cellulases of *Trichoderma* and by integrating heterologous genes to a locus with high expression and production levels.

The present invention relates also to a method for producing the variant of the invention. The production medium used in culturing the host cell may be a medium suitable for growing the host organism and containing inducers for efficient gene expression.

The present invention also relates to an enzyme composition comprising the variant of the invention. As used in the present context the "enzyme preparation" or "enzyme composition" refers to any enzyme product, preparation or composition, which comprises at least one of the variants of the present invention. An enzyme composition may be a spent culture medium or filtrate containing one or more variant, or one or more variant and one or more other enzymes. "Spent culture medium" means the culture medium of the host comprising the produced enzymes. Preferably the host cells are separated from said medium after the production. The enzyme preparation or composition may be a "whole culture broth" obtained, optionally after inactivating the production host(s) or microorganism(s) without any biomass separation, down-stream processing or purification of the desired cellulolytic enzyme(s), because the present variants can be secreted into the culture medium, and they display activity in the ambient conditions of the spent culture medium.

The enzyme composition may contain the enzymes in at least partially purified and isolated form. It may even essentially consist of the desired enzyme or enzymes. If desired, the enzyme compositions may be dried, spray-dried or lyophilized, granulated or the enzymatic activity may be otherwise concentrated and/or stabilized for storage. If required, a desired enzyme may be crystallized or isolated or purified in accordance with conventional methods, such as filtration, extraction, precipitation, chromatography, affinity chromatography, electrophoresis, or the like.

In addition to one or more variants of the present invention, the enzyme composition may comprise one or more other enzymes additional enzymes selected from the group consisting of protease, lipase, cutinase, amylase, carbohydrase, cellulase, pectinase, pectatelyase, pectinolytic enzyme, esterase, phytase, mannanase, arabinase, galactanase, xylanase, oxidase, xanthanase, xyloglucanase, nuclease, laccase, and/or peroxidase, preferably selected from the group consisting of proteases, amylases, cellulases and lipases., More specifically, the enzyme preparation may comprise at least one further enzyme selected from a group of cellobiohydrolase, endoglucanase, beta-glucanase, beta-glucosidase, serine protease, xylanase, beta-xylosidase, mannanase, beta-mannosidase, endopectinlyase, pectate lyase, pectinesterase, laccase, cutinase, peroxidase and copper-dependent lytic polysaccharide monooxygenase i.e. glycosyl hydrolase family 61 (GH61) or Auxiliary Activity family 9 (AA9) enzymes. The enzyme composition may contain any combination of these enzymes and the variants of the invention, but the enzymes are not limited to those described herein. The additional enzymes can, for example, also be commercially available enzyme preparations. It depends on the application what other enzymes are included in the enzyme composition or used in the enzyme treatment.

The present enzyme composition comprising cellulase and an additional enzyme may be advantageous in providing synergistic effects. Such additional enzymes are desired when the present enzyme composition comprising cellulase is used in detergents e.g. when washing stains. Particularly advantageous synergistic enzymes that work with cellulases are amylases, proteases and mannanases, or a combination thereof. The perfect combination of enzymes allows maximal performance.

In general the properties of the selected enzyme(s) should be compatible with the selected detergent, (i.e., pH-optimum, compatibility with other enzymatic and non-enzymatic ingredients, etc.), and the enzyme(s) should be present in effective amounts. The enzyme composition may comprise the variant of the invention and:

a. optionally at least one polyol selected from propylene glycol, glycerol, a sugar, sugar alcohol, sorbitol, hexylene glycol, b. at least one preservative selected for example from organic acids, e.g. benzoic acid, citric acid, ascorbic acid, sorbic acid, and salts thereof, sodium benzoate, hydroxybenzoate, benzisothiazolinone (BIT) or a combination thereof;

c. optionally at least one inhibitor selected from formic acid, lactic acid, boric acid, boric acid derivative, aromatic borate ester, phenyl boronic acid derivative, peptide, other reversible subtilisin inhibitors or a combination thereof;

d. optionally at least one enzyme selected from proteases, amylases, cellulases, lipases, xylanases, mannanases, cutinases, esterases, phytases, nucleases, pectinases, pectinolytic enzymes, pectate lyases, carbohydrases, arabinases, galactanases, xanthanases, xyloglucanase, laccases, peroxidases and oxidases with or without a mediator, or a combination thereof;

e. optionally at least one salt selected from sodium chloride, potassium chloride, potassium (hydrogen) phosphate, sodium (hydrogen)phosphate, ammonium sulfate, potassium sulfate, or a combination thereof; and f. optionally at least one filler or carrier selected from maltodextrin, flour, sodium chloride, sulfate, sodium sulfate, sodium acid pyrophosphate, tetrasodium pyrophosphate, polyethylene glycol, or a combination thereof.

The additional components a-f provide improved properties for the present enzyme composition. The enzyme composition is compatible with the additional components and improves applicability of the enzyme composition in various uses. Salts, such as sodium chloride and sodium sulfate function as drying aids. In an embodiment the present enzyme composition is in the form of a liquid composition or a solid composition such as solution, dispersion, paste, powder, granule, granulate, coated granulate, tablet, cake, crystal, crystal slurry, gel or pellet. The enzyme composition can be used in cleaning agents or boosters that are added on top of the detergent during or before the wash and that are for example in the form of liquid, gel, powder, granules or tablets. The enzyme composition and detergent components may also be soaked in a carrier like textiles.

In an embodiment the enzyme composition is used in textile and detergent industry, biomass processing and biomass hydrolysis, preferably in biofuel, starch, pulp and paper, food, baking, feed or beverage industries.

The present invention relates further to a detergent composition comprising at least one of the novel variant cellulase polypeptides or an enzyme composition thereof. The invention relates also to a use of the variant cellulase polypeptides of the invention in detergent applications. The terms "detergent composition" and "detergent" include, unless otherwise indicated, all washing agents in any form such as solid, granular or powder-form, liquid, gel or paste-form, and any combination thereof. The detergent composition may be in the form of a sachet, pouch, tablet or bar, including multi-compartment products. The detergent composition can be a free-flowing powder or a liquid. The terms include, unless otherwise stated, all-purpose or heavy-duty washing agents, especially cleaning detergents; liquid fine-fabric, specialty or low-duty detergents; hand dishwashing agents or light duty dishwashing agents, especially those of the high-foaming type; machine dishwashing agents, including the various tablet, granular, liquid and rinseaid types for household and institutional use; liquid cleaning and disinfecting agents, car or carpet shampoos, bathroom cleaners; metal cleaners; as well as cleaning auxiliaries such as bleach additives and "stain-stick" or pretreat types, and laundry aids.

The terms "detergent", "detergent composition" and "detergent formulation" are used in reference to mixtures, which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. It is intended that in addition to the cellulase variants according to the invention, the term encompasses detergents that may contain e.g., surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, buffers, preservatives, sod suppressors, solvents, and structurants for liquid detergents, structure elasticizing agents, enzyme inhibitors or stabilizers, enzyme activators, transferase(s), hydrolytic enzymes, oxido reductases, bluing agents and fluorescent dyes, antioxidants, and solubilizers.

The detergent composition of the invention may comprise one or more components selected from the group consisting of anionic surfactants (0-40% by weight), nonionic surfactants (0-40% by weight), and phosphonates (0-15% by weight) in addition to the effective amount of the variant cellulase polypeptide or an enzyme preparation thereof.

The term "effective amount" of a variant cellulase polypeptide refers to the quantity of the enzyme necessary to perform sufficiently in the specific detergent application. The amount of enzyme preparation in a detergent composition may vary depending on type and concentration of the detergent. Preferably the detergent composition comprises from about 0.000001% to about 10% by weight of the detergent composition of a variant cellulase polypeptide of the invention, more preferably from 0.00005% to about 1%, even more preferably from 0.00001% to 0.1%.

The detergent composition may be in the form of a bar, a homogenous tablet, a tablet having two or more layers, a pouch having one or more compartments, a regular or compact powder, a granule, a paste, a gel, or a regular, compact or concentrated liquid. In one embodiment the detergent composition can be a laundry detergent composition, preferably a liquid or solid laundry detergent composition. There are a number of detergent formulation forms such as layers (same or different phases), pouches, as well as forms for machine dosing unit.

The present variant or the enzyme composition may be added directly into a detergent or it can be applied separately on top of the detergent during or before wash, or, for example, in liquid/liquid or liquid/powder sachets or multicompartment sachets or bottles, in which it may be separated from some of the detergent components or other enzymes, like protease, to maximize the storage stability.

The term "stability" includes storage stability and stability during use, e.g. during a wash process (in wash stability) and reflects the stability of the variant cellulase according to the invention as a function of time, e.g. how much activity and/or wash performance is retained when the variant cellulase is kept in solution, in particular in a detergent solution. The stability is influenced by many factors, e.g. pH, temperature, detergent composition e.g. proteases, stabilizers, builders, surfactants etc. The variant cellulase stability may be measured using the activity assays or more preferably the application tests described in examples. In a preferred embodiment stability includes the meaning of stability in the presence of proteases.

The variant of the present invention or the present enzyme composition can also be used in cleaning agents or boosters that are added on top of the detergent during or before the wash and that are for example in the form of liquid, gel, powder, granules or tablets. The enzyme composition and detergent components may also be soaked in a carrier like textiles.

The present variant and the enzyme composition may be used for treating any cellulosic material. In the present context, "cellulosic material" refers to any material comprising cellulose or derivatives thereof as a significant component. Such a material may be textile material, plants or material of plant origin used in food or animal feed, plant material for oil extraction, or wood-derived mechanical or chemical pulp or secondary fiber. The present variant is especially useful in the treatment of textile materials. The term "textile" means any textile material including yarns, yarn intermediates, fibers, non-woven materials, natural materials, synthetic materials, and any other textile material, fabrics made of these materials and products made from fabrics (e.g., garments, linen and other articles). The textile or fabric may be in the form of knits, wovens, denims, nonwovens, felts, yarns, and towelling. The textile may be cellulose based, such as natural cellulosics including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabbit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained house-hold laundry. When the term fabric or garment is used it is intended to include the broader term textiles as well.

By "denim" is meant, in connection of this invention, denim fabric, usually denim garments, particularly jeans. Advantageously, the denim is Indigo dyed denim. Denim can also be treated with derivatives of Indigo or with Indigo together with some other dye, for example, Indigo-dyed denim with sulphur bottom.

The cellulosic material is reacted with the variant of the invention or the present enzyme composition comprising said variant under suitable conditions, such as appropriate pH, and temperature, and the reaction is allowed to continue for a time sufficient for the enzymatic reaction to take place, whereby at least partially hydrolyzed cellulosic material is obtained. The enzymes are added in an enzymatically effective amount either simultaneously e.g. in the form of an enzyme mixture, or sequentially.

As used herein, the term "antigreying performance" or "antigreying effects" mean antiredepositioning and pigment removal properties. With increasing number of wash cycles, pigments, particles and soluble soils, salts and other material can adhere on the textile fibers, most likely in areas with damaged cotton fibers. This can cause a greying effect and a darkening or yellowing of the cotton textile. Suitable test methods are generally known in the art and are typically based on using artificial ballast soil systems with standard white test fabrics in repeated washing cycles in washing machines. The antigreying effect can be tested also by a single wash as stressed test using redeposition liquid based on carbon black. In an embodiment the antigreying effect is determined according to Example 5.

The variant may be added into detergent compositions to improve fiber and color care properties by prevention and removal of fuzz and pills resulting in brightening or freshening of colors and softening, and to improve textile cleaning. The terms "depilling" (removal of pilling) and "color revival" are typically used to describe the cellulase effects on old, used cotton textiles. The terms "antipilling" (prevention of pilling), "color maintenance" or "color care" are typically used to describe cellulase effects on new garments.

As used in the present context the expression "cellulase performance" in detergent application refers to the effect of cellulase on the fiber and color care properties of detergent, that can be measured as a visible and measurable decrease of lightness (i.e. increase of darkness) or change in color of colored cotton textiles. When the surface fibers and fibrils protruding from the yarn forming pills and giving the fabric a "greyish" or worn out look are removed by cellulase, the lightness of the fabric decreases, and the surface of the fabric appears darker and colors get brighter. Lightness or change in color values can be measured, for example by measuring the color as reflectance values with a spectrophotometer using $L^*a^*b^*$ color space coordinates as described in Examples. Cellulase performance is for example calculated as $\Delta L^*$(delta $L^*$), which means lightness value $L^*$ of enzyme treated fabric minus lightness value $L^*$ of fabric treated with washing liquor without cellulase enzyme (enzyme blank, control). When the test material is consisting of textiles with different colors (e.g. commercially available pilling monitors containing 4 stripes), the total cellulase performance is calculated as a sum of ΔL* of each color after several washing cycles and the final results are shown as increase of darkness (sum of –ΔL*).

The present variant and the enzyme composition are especially useful in finishing processes of the textile industry, such as biofinishing of fabrics, garments or yarn. As used in the present context, the expression "biofinishing" (also called depilling, defuzzing, dehairing or biopolishing) refers to the use of the variant enzymes in a controlled hydrolysis of cellulosic fibers in order to modify the fabric or yarn surface in a manner that permanently prevents the tendency for pilling, improves fabric handle like softness and smoothness, clears the surface structure by reducing fuzzing. Biofinishing results in clarification of colors, improves the drapability of the fabric and improves moisture absorbability, which may further improve also the dyeability. Biofinishing may be performed before, after or at the same time as dyeing.

Enzymatic depilling can be carried out at any stage during textile wet processing, preferably after optional desizing and/or bleaching, and similar conditions as in biostoning can be used. Also textiles in garment form can be treated.

The present variant and enzyme preparation may be used in biostoning of denim. As used in the present context, the expression "biostoning" of fabric or garment means the use of enzymes in place of, or in addition to, pumice stones for the treatment of fabric or garment, especially denim to obtain an aged or worn look. The term "aged or worn look" means that as a result of uneven dye removal, there are contrasts between dyed areas and areas from which dye has been removed.

The liquor ratio (the ratio of the volume of liquid per weight of fabric) in both biostoning and biofinishing may range from about 3:1 to 20:1, preferably 5:1 to 10:1. The treatment time can vary between 15 min to 90 min and preferably between 30 min to 60 min. It should be emphasized that the enzyme dosage greatly depends on the type of the fabrics, machinery, process conditions (pH, temperature, liquor ratio, treatment time, denim load, process scale) and type of the enzyme preparation or composition. Typical process parameters for e.g. industrial biofinishing are pH 4.5-8 at temperature of 40-65° C. The variant cellulase polypeptides of the invention show performance at a wide range of pH and temperature conditions. A person skilled in art is capable in defining suitable dosages and conditions.

The present variants and enzyme preparations/compositions or detergent compositions containing them provide unexpected advantages when used in detergent and textile industries. The variants of the invention have considerably better stability in a detergent/detergent composition than cellulases of the prior art, even in the presence of a protease. In detergent applications, the variants of the invention have considerably improved stability measured as color revival (pilling removal). The present variants are also efficient in antigreying.

It will be obvious to a person skilled in the art that, as the technology advances, the inventive concept can be implemented in various ways. The invention and its embodiments are not limited to the examples described but may vary within the scope of the claims.

EXAMPLES

Example 1. Production of *Acremonium thermophilum* ACM88 Cellulase Variants in *Trichoderma reesei*

Standard molecular biology methods were used in the isolation and enzyme treatments of DNA (e.g. isolation of plasmid DNA, digestion of DNA to produce DNA fragments), in *E. coli* transformations, sequencing etc. The basic laboratory methods used were either as described by the enzyme, reagent or kit manufacturer or as described in the standard molecular biology handbooks, e.g. Sambrook and Russell (2001) or as described in the following examples.

Cellulase variants were derived from a parental molecule, designated as ACM88 (described in WO2016/066896). The catalytic core in ACM88 derives from *A. thermophilum* Cel45A. The signal sequence and the linker and CBM region derive from *T. reesei* Cel7A. The full-length nucleic acid sequence of ACM88 is presented as SEQ ID NO: 3 and the corresponding amino acid sequence as SEQ ID NO: 2. The nucleotide sequence (SEQ ID NO: 2) contains introns at positions 72-130 and 380-502. The mature amino acid sequence of ACM88 (without signal sequence) is presented as SEQ ID NO: 1.

Expression plasmids were constructed for production of recombinant ACM88 variants. The constructs contain *T. reesei* cel7A promoter and the amdS marker gene as described in Paloheimo et al. 2003. Synthetic genes (Table 1), including mutations introduced in the coding region of the parental molecule, were exactly fused as SacII-BamHI fragments to the *T. reesei* cel7A promoter by ligation. For transcription termination *T. reesei* cel7A or *T. reesei* cel6A terminator was used (FIG. 1). Type of expression plasmid used for each variant is listed in Table 1. A linear expression cassette was isolated from the vector backbone by NotI or EcoRI digestion, or circular plasmid was used directly in transformation of *T. reesei* protoplasts and transformants were selected with acetamide as sole nitrogen source. The host strain lacks the four major endogenous cellulases: CBHI/Cel7A, CBHII/Cel6A, EGI/Cel7B and EGII/Cel5A. The transformations were performed according to Penttilä et al, 1987, with the modifications described in Karhunen et al., 1993.

TABLE 1

Cellulase variants deriving from parental molecule ACM88. Expression plasmid type used in the expression of the recombinant cellulase is shown (FIG. 1).

| Variant name | Mutation | Expression plasmid type |
|---|---|---|
| DC1 | S23R, V24M | 1 |
| DC2 | S136H, V24I | 1 |
| DC3 | Y146W, Q184H | 1 |
| DC4 | N66Q, T59I | 1 |
| DC5 | A56M, Q167A | 1 |
| DC6 | S153R, A43R | 1 |

TABLE 1-continued

Cellulase variants deriving from parental molecule ACM88. Expression plasmid type used in the expression of the recombinant cellulase is shown (FIG. 1).

| Variant name | Mutation | Expression plasmid type |
|---|---|---|
| DC7 | K44R, D48E | 1 |
| DC8 | A77S, Q167Y | 1 |
| DC9 | A122M, Q137M | 1 |
| DC10 | G17C, V28C | 1 |
| DC11 | K21R, A43R | 1 |
| DC12 | S156R, K44R | 1 |
| DC13 | I130N, A144Q | 1 |
| DC14 | S190V, T180E | 1 |
| DC15 | Y69K, E191D | 1 |
| DC16 | V208D, F209W | 1 |
| DC17 | K44Q, D48T | 1 |
| DC18 | S54M, T108I | 1 |
| DC19 | S30L, D40E | 1 |
| DC20 | A43R, D48T | 1 |
| DC21 | D65E, N66Q | 1 |
| DC22 | T92E, Q184R | 1 |
| DC23 | S23P, T193I | 1 |
| DC24 | D151S, P164Q | 1 |
| DC25 | N66S, D40N, N42S | 1 |
| DC26 | T229N, S241Q | 1 |
| DC27 | H249R, I256R | 1 |
| DC28 | P261H, Y277W | 1 |
| DC29 | A33K, G112A | 1 |
| DC30 | Q82T | 1 |
| DC31 | Q82R, E116H | 1 |
| DC32 | A56C, P161C | 1 |
| DC33 | E81D, T110H | 1 |
| DC34 | K4H, S116D | 1 |
| DC36 | Q252E, Y258H | 1 |
| DC37 | S217Q, N220Q | 1 |
| DC38 | N220E, N225Q | 1 |
| DC39 | Y258H, A265Q | 1 |
| DC40 | V263Q, A265Q | 1 |
| DC41 | Del G78 | 1 |
| DC42 | A33Q, A75S | 1 |
| DC43 | A99S, G133A | 1 |
| DC44 | P161S, A204N | 1 |
| DC45 | P164T, Q184E | 1 |
| DC46 | A33Q, A99S, P161S, P164T, Q184E | 1 |
| DC47 | H249K, S248H | 1 |
| DC48 | F131H | 1 |
| DC49 | A122G | 1 |
| DC50 | A122S | 1 |
| DC51 | S23P, D65E, N66Q, A77S, Q82T, Q167Y, T193I | 1 |
| DC52 | K44Q, D48T, T92E, S109N, Q184R | 1 |
| DC53 | D65E, N66Q, S217Q, N220Q, T229N, S241Q | 1 |
| DC54 | S23P, D65E, N66Q, Q82T, T193I | 1 |
| DC55 | S23R, A77S, Q82T, Q167Y, T193I | 1 |
| DC56 | D65E, N66Q, T92E, Q184R | 1 |
| DC57 | K44N, D48S | 1 |
| DC58 | S23P, A77S, H249R | 1 |
| DC59 | Q167Y, T193I, I256R | 1 |
| DC60 | S217T, N220E | 1 |
| DC61 | S217D, N220E, N225D, T229D, G244S | 1 |
| DC62 | S217G, N220G, N225G, G244S | 1 |
| DC63 | S248W, G254L | 1 |
| DC64 | T262R, G267A | 1 |
| DC65 | Q271I, L273I | 1 |
| DC66 | V272Q, S248N | 1 |
| DC67 | G254R, T262I | 1 |
| DC68 | Q271R, L273Q | 1 |
| DC69 | N51E, A33R | 1 |
| DC70 | S23P, K44N, D48S, D65E, N66Q, A77S, Q167Y, T193I, H249R, S15T, A22T, T92A | 1 |
| DC71 | S23P, K44N, D48S, D65E, N66Q, A77S, Q167Y, T193I, H249R, D113A | 1 |
| DC72 | S23P, K44N, D48S, D65E, N66Q, A77S, Q167Y, T193I, H249R, G143A, Q145E | 1 |
| DC73 | S23P, K44N, D48S, D65E, N66Q, A77S, Q167Y, T193I, H249R, Q174E, N178D | 1 |
| DC74 | N210Q, N215S, N220E, N225S | 1 |
| DC75 | P211I, P216T, N220E, P226T | 1 |
| DC76 | R233S, R234S | 1 |
| DC77 | N210E, N215S, N220E, N225S | 1 |

TABLE 1-continued

Cellulase variants deriving from parental molecule ACM88. Expression plasmid type used in the expression of the recombinant cellulase is shown (FIG. 1).

| Variant name | Mutation | Expression plasmid type |
|---|---|---|
| DC78 | N210S, N215S, N220S, N225S | 1 |
| DC79 | P211T, P216T, P221T, P226T | 1 |
| DC80 | P211T, N215S, P221T, P226T | 1 |
| DC81 | N210T, N215T, N220E, N225T | 1 |
| DC82 | N210Q, P211A, N215S, P216S, N220E, P221A, N225S, P226A | 1 |
| DC83 | N210Q, P211A, N215S, P216T, N220Q, P221A, N225S, P226T | 1 |
| DC84 | N210S, P211T, N215S, P216T, N220S, P221T, N225S, P226T | 1 |
| DC85 | P211T, P221S, P222S | 1 |
| DC86 | P226S, P227T | 1 |
| DC87 | S23P, K44N, D48S, D65E, N66Q, A77S, Q167Y, T193I, H249R | 1 |
| DC88 | S23P, K44N, D48S, D65E, N66Q, A77S, Q167Y, T193I, H249R, A265H, Q271V | 1 |
| DC89 | S23P, K44N, D48S, D65E, N66Q, A77S, Q167Y, T193I, P211T, N215S, P221T, P226T, H249R | 1 |
| DC90 | Del N210-N220 | 1 |
| DC91 | Del N210-N215 | 1 |
| DC92 | Del N210, Del N215 | 1 |
| DC93 | Del N210 | 1 |
| DC94 | S23P, K44N, D48S, D65E, N66Q, A77S, Q167Y, T193I, N210T, H249R | 1 |
| DC95 | S23P, K44N, D48S, D65E, N66Q, A77S, Q167Y, T193I, N220T, P245C, H249R, P261C | 1 |
| DC96 | S23P, K44N, D48S, D65E, N66Q, A77S, Q167Y, T193I | 1 |
| DC97 | A19R | 1 |
| DC98 | Q82R | 1 |
| DC99 | N210W | 1 |
| DC100 | N215R | 1 |
| DC101 | N225D | 1 |
| DC102 | R234M | 1 |
| DC103 | G244T | 1 |
| DC104 | S266E | 1 |
| DC105 | A19R, Q82R | 1 |
| DC106 | N210W, N215R, N225D | 1 |
| DC107 | R234M, G244T, S266E | 1 |
| DC108 | A19R, Q82R, N210W, N215R, N225D, R234M, G244T, S266E | 1 |
| DC109 | K44N, D48S, D65E, N66Q, A77S, Q167Y, T193I | 2 |
| DC110 | S23P, D48S, D65E, N66Q, A77S, Q167Y, T193I | 2 |
| DC111 | S23P, K44N, D65E, N66Q, A77S, Q167Y, T193I | 2 |
| DC112 | S23P, K44N, D48S, A77S, Q167Y, T193I | 2 |
| DC113 | S23P, K44N, D48S, D65E, N66Q, Q167Y, T193I | 2 |
| DC114 | S23P, K44N, D48S, D65E, N66Q, A77S, T193I | 2 |
| DC115 | S23P, K44N, D48S, D65E, N66Q, A77S, Q167Y | 2 |
| DC116 | A19R, G244T, S266E | 2 |
| DC117 | N210S, N215S, N220S, N225S, R234P, G244T | 2 |
| DC118 | N210S, N215S, N220S, N225S, R234M, G244T | 2 |
| DC119 | N210S, N215S, N220S, N225S, G244T | 2 |
| DC120 | N210T, N215T, N220T, N225T, G244T | 2 |
| DC121 | N210S, N215R, N220S, N225S | 2 |
| DC122 | DelN210-N215, N220S, N225S, R234M, G244T | 2 |
| DC123 | DelN210, N220S, N225S, R234P, G244T | 2 |
| DC124 | DelN210, N220S, N225S, G244T | 2 |
| DC125 | N210S, N215S, R234M, G244T | 2 |
| DC126 | N210S, N215R, G244T | 2 |
| DC127 | N210S, N215S, G244T | 2 |
| DC128 | N210S, G244T | 2 |
| DC129 | S23P, D65E, N66Q, A77S, N210S, N215S, N220S, N225S, G244T | 2 |
| DC130 | S23P, D65E, N66Q, A77S, T108I, N210S, N215S, N220S, N225S, G244T | 2 |
| DC131 | S23P, Q58H, D65E, N66Q, A77S, N210S, N215S, N220S, N225S, G244T | 2 |
| DC132 | S23P, D65E, N66Q, A77S, Q82T, N210S, N215S, N220S, N225S, G244T | 2 |
| DC133 | S23P, D65E, N66Q, A77S, Q167Y, N210S, N215S, N220S, N225S, G244T | 2 |
| DC134 | S23P, K44N, D48S, D65E, N66Q, A77S, N210S, N215S, N220S, N225S, G244T | 2 |
| DC135 | K44N, D48S, D65E, N66Q, N210S, N215S, N220S, N225S, G244T | 2 |
| DC136 | S23P, K44N, D48S, A77S, N210S, N215S, N220S, N225S, G244T | 2 |
| DC137 | S23P, A77S, N210S, N215S, N220S, N225S, G244T | 2 |
| DC138 | D65E, N66Q, N210S, N215S, N220S, N225S, G244T | 2 |
| DC139 | Q167Y, N210S, N215S, N220S, N225S, G244T | 2 |
| DC140 | S23P, K44N, D48S, A77S, Q167Y N210S, N215S, N220S, | 2 |

TABLE 1-continued

Cellulase variants deriving from parental molecule ACM88. Expression plasmid
type used in the expression of the recombinant cellulase is shown (FIG. 1).

| Variant name | Mutation | Expression plasmid type |
|---|---|---|
| | N225S, G244T | |
| DC141 | S23P, K44N, D48S, D65E, N66Q, A77S, Q167Y, N210S, N215S, N220S, N225S, G244T | 2 |
| DC142 | S23P, D65E, N66Q, A77S, N210S, N215S, N220S, N225S, R234P, G244T | 2 |
| DC143 | S23P, K44N, Q167Y, N210S, N215S, N220S, N225S, G244T | 2 |
| DC144 | S23P, D65E, N66Q, A77S, Q167Y, N210S, N215R, N220S, N225S | 1 |
| DC145 | S23P, D65E, N66Q, A77S, Q167Y, N210S, N215R, N220S, N225S, G244T | 1 |
| DC146 | S23P, D65E, N66Q, A77S, Q167Y, N210S, N215R, G219S, N220S, N225S, G244T | 1 |
| DC147 | S23P, D65E, N66Q, A77S, Q167Y, N210S, N215R, N220S, N225S, S242G | 1 |
| DC148 | S23P, D65E, N66Q, A77S, Q167Y, T193V, N210S, N215R, N220S, N225S | 1 |
| DC149 | D65E, N66Q, A77S, Q167Y, N210S, N215R, N220S, N225S | 1 |
| DC150 | Q167Y, N210S, N215R, N220S, N225S | 1 |
| DC151 | S23P, Q167Y, N210S, N215R, N220S, N225S | 1 |
| DC152 | S23P, K44N, Q167Y, N210S, N215R, N220S, N225S | 1 |

The endoglucanase production of the transformants was analyzed with an activity assay from the culture supernatants of shake flask cultivations (50 ml). The transformants were grown for 7 days in a complex cellulase-inducing medium (Joutsjoki et al., 1993) buffered with 5% $KH_2PO_4$ at pH 5.5. The enzyme activity of the recombinant protein was measured from the culture supernatant as the release of reducing sugars from carboxymethylcellulose (3% CMC) at 50° C. in 50 mM HEPES buffer, pH 7.0 essentially as described by Bailey and Nevalainen, 1981; Haakana et al, 2004 (NCU activity). In addition to NCU activity, endoglucanase activity was determined for selected variants using activity assay containing substrate Azo-Alpha-Cellulose (I-ACELL, Megazyme International Ireland Ltd) or Azo-CM-Cellulose (S-ACMC, Megazyme International Ireland Ltd). Production of the recombinant protein was also detected from the culture supernatant by sodium dodecyl sulfate polyacrylamide gel electrophoresis (SDS-PAGE).

Chosen transformants and the reference strain producing the parental ACM88 cellulase were cultivated in shake flasks or bioreactors in complex cellulase-inducing medium to obtain material for application tests (Examples 2 to 4).

Example 2. Testing the Color Revival Performance of *Acremonium thermophilum* Cel45A ACM88 Variants in in Launder-Ometer Enzyme preparations of *Acremonium thermophilum* Cel45A ACM88 variants produced in *Trichoderma* as described in Example 1, showing improved stability in detergent solution as enzyme activity with soluble substrates CMC or Azo-CM-Cellulose and/or with insoluble substrate Azo-Alpha-Cellulose in short-term stability tests at elevated temperatures, were chosen for application tests. The performance of variants was tested in commercial detergent as color revival (depilling) effect. ACM88 was used for comparison.

Color revival effect was tested using prepilled/predamaged monitors E-253 of multicolor printed Jersey (94% Cotton, 6% Dorlastan) supplied from Center For Testmaterials BV (The Netherlands). Prepilled monitors E-253 were used for the demonstration of the removal of pilling (depilling) from material representing used cotton textiles. The same predamaged monitors were also used for demonstration of the color revival effect of used colored textiles. Fabrics were cut into swatches (approx. 29 cm×15-16.5 cm, total weight of two swatches approx. 24 g) containing full width stripes of each color (black, red, green, blue) and the edges were neatened.

Cellulase treatments were performed in Atlas LP-2 Launder-Ometer as follows. Launder-Ometer was first preheated to 40° C. 60 g of steel balls (diameter 0.6 cm), 240 ml of wash liquor and diluted enzyme (<1.0 ml) were added into 1.2 liter containers. After that, 2 swatches of E-253 were placed in containers (reverse side on reverse side) and the Launder-Ometer was run at 40° C. for 60 min with a rotation speed of 42 rpm.

Enzymes were dosed as 2 activity units (NCU) per ml of wash liquor. Activity was measured as described in Example 1. The wash liquor contained 4.4 g of Commercial liquid detergent (Table 2, Example 3) per litre of synthetic tap water (16° dH) and its pH was approx. 8.5. Protease Savinase 16 L (Novozymes) had been added to detergent 0.7% w/w.

For synthetic tap water with hardness of 16° dH the following stock solutions were prepared in deionized water (Milli-Q or equivalent):
Stock solution with 1000° d Calcium-hardness: $CaCl_2$× $2H_2O$ (1.02382.1000, Merck KGaA, Germany) 26.22 g/l
Stock solution with 200° d Magnesium-hardness: $MgSO_4$×7 $H_2O$ (1.05886.1000, Merck KGaA, Germany) 8.79 g/l $H_2O$ $NaHCO_3$ stock solution: $NaHCO_3$ (1.06329.1000 Merck KGaA, Germany) 29.6 g/l.

13.3 ml $CaCl_2$) solution, 13.3 ml $MgSO_4$ solution and 10.0 ml of freshly made $NaHCO_3$ solution were added in volumetric flask in the given order, made up to 1 liter with deionized water and mixed. The hardness of water was determined by complexometric titration and found correct.

After the cellulase treatment in Launder-Ometer, the swatches were first rinsed separately under running water (ca. 20° C.) and then in a washing machine (Whirlpool) using rinsing program with extraction. Swatches were dried in a tumbler. Washing and tumbling cycles were repeated 3 times.

The cellulase performance in detergent was evaluated by measuring the color as reflectance values with Konica Minolta CM-3610A spectrophotometer using L*a*b* color space coordinates (illuminant D65/10°, 420 nm cut). The color of each 4 stripes of test monitors was measured after 3 washing cycles. Decrease of lightness (L*), i.e. increase of darkness compared to treatment without cellulase, was used as an indication of cellulase effect. When the surface fibers and fibrils protruding from the yarn forming pills and giving the fabric a greyish look, are removed by cellulase, the lightness of the fabric decreases, and the surface of the fabric appears darker and colors get brighter. The color was measured from the swatches also before the cellulase treatment to select homogenous material for the tests.

Cellulase performance was calculated as $\Delta L^*$(delta L*), which means lightness value L* of enzyme treated fabric minus lightness value L* of fabric treated with washing liquor without cellulase enzyme (enzyme blank, control). Sum of $\Delta L^*$ for each 4 stripes was calculated and the final results were shown as increase of darkness ($-\Delta L^*$).

Figure 2A:
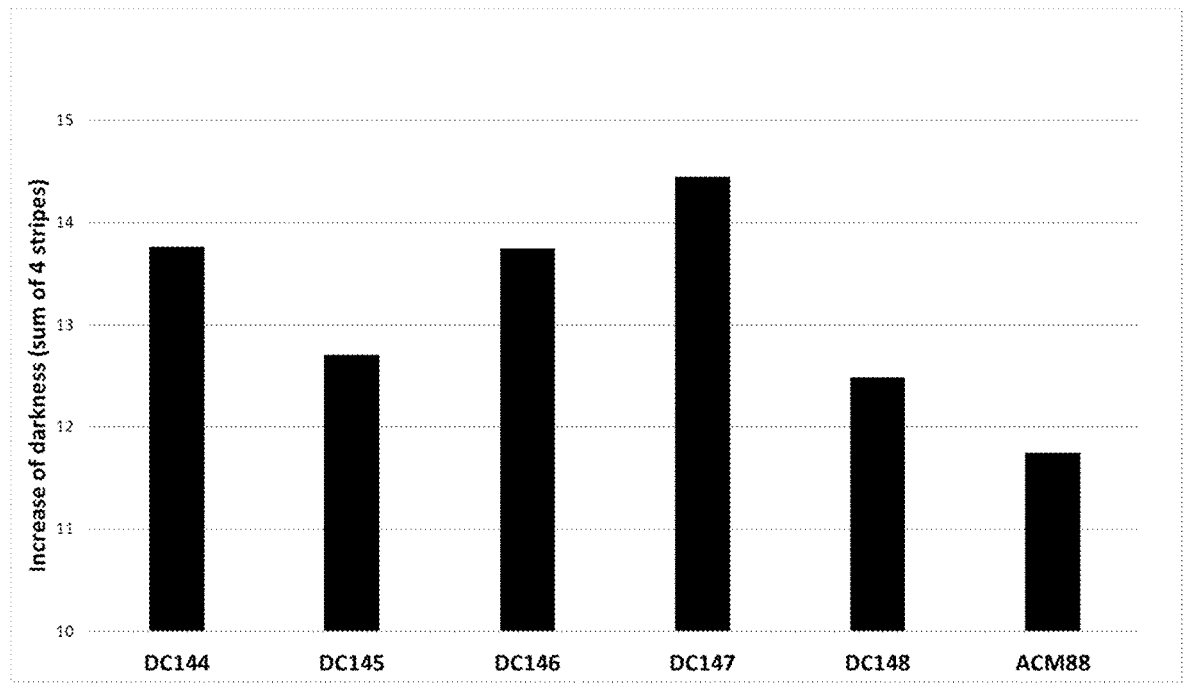
FIGS. 2A and 2B show the color revival (pilling removal/depilling) performance of the variants compared to ACM88 as an increase of darkness (sum of −ΔL* of 4 stripes) after 3 washing and tumbling cycles of test monitors (E-253). Washing conditions in Launder-Ometer were: 40° C., 60 min, 16° dH, detergent 4.4 g/l, pH ~8.4, enzyme dosage 2 NCU/ml.
Figure 2B:
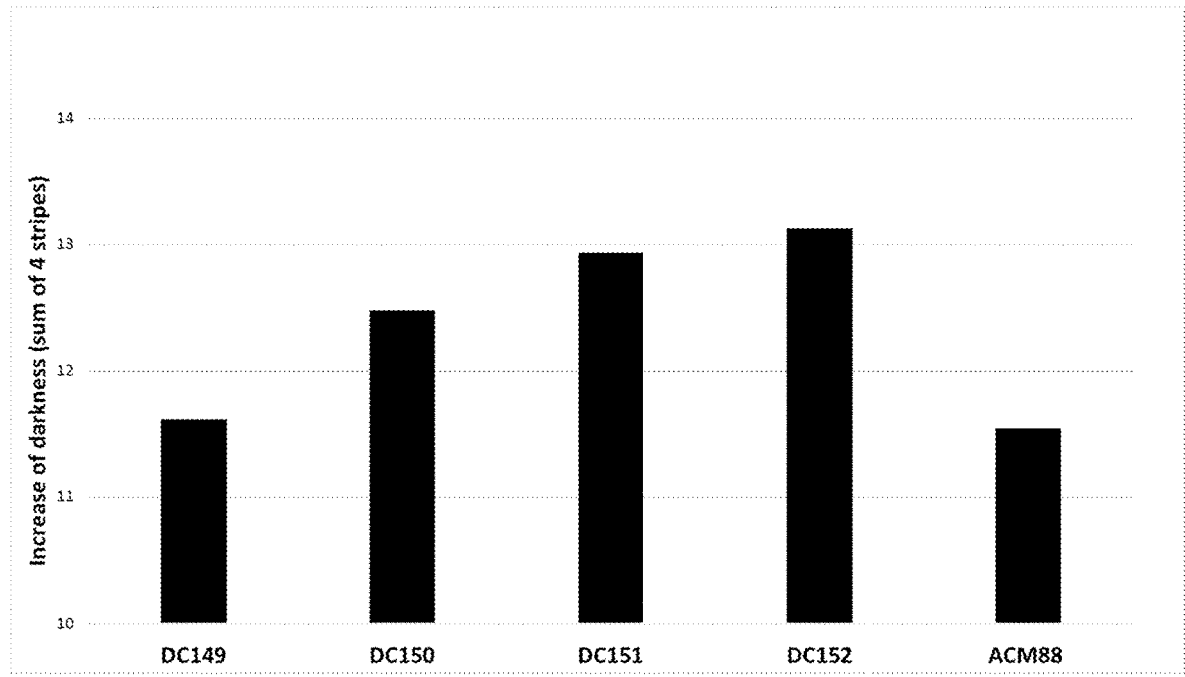

Results of the variants DC144-DC148 are shown in FIG. 2A and variants DC149-DC152 in FIG. 2B. Variants DC145, DC148, DC150, DC151 and especially the variants DC144, D146, DC147, and DC152 showed better performance measured as color revival/depilling effect. The spectrophotometrical results were also confirmed by visual evaluation. Prepilled/predamaged fabric, which appeared worn and uninteresting, regained its original look even better with the variants than with ACM88. Also variants DC133, DC139, DC140 and DC 141 had slightly improved depilling performance compared to ACM88 (data not shown).

Tests with variants DC146 and DC150 were carried out also using a similar test system as described above but having 10 repeated washing and tumbling cycles and smaller enzyme dosages (0.05-0.2 NCU/ml wash liquor), representing a typical dosing range of commercial cellulase product if dosages were calculated as % of detergent weight. In these tests unpilled, original fabric (E-252, Center For Testmaterials BV) was used in addition to prepilled monitors (E-253). Monitors of original fabric were used for the demonstration of the color maintenance/color care and/or prevention of pilling (antipilling) effect of new fabrics. In addition to high depilling effect, DC146 and DC150 had also improved color care/antipilling effect compared to parental ACM88 (data not shown).

Example 3. Testing the Stability of *Acremonium thermophilum* Ce145A ACM88 Variants in Detergent Measured as Color Revival (Depilling) Performance The stability of the most promising candidates of *Acremonium thermophilum* Cel45A ACM88 variants identified in Example 1 was tested by application tests as color revival (depilling effect) using similar test system as described in Example 2. ACM88 was used for comparison.

A 0.7% w/w amount of protease, Savinase 16L (Novozymes), was added to a commercial liquid detergent containing no enzymes. The composition of detergent is described in Table 2. Cellulases were initially added in detergent in such amount that dosages would be 2 (or 3) activity units (NCU) per ml of wash solution. Activity was measured as described in Example 1 except using extended reaction time of 30 min. Samples in plastic tubes with caps were incubated at room temperature (approx. 20-22° C.) for 4 (or 3) days. The performance of stored samples was compared to washes, in which the cellulases had been added fresh into washing liquor containing detergent and same amount of protease that was initially added to the stored samples, corresponding to initial performance at timepoint 0. Results were calculated as residual performance (%), which was obtained by dividing the performance of sample after storage by the initial performance (fresh performance) of the sample.

TABLE 2

| Composition of commercial liquid detergent | |
|---|---|
| Ingredient | % |
| Anionic surfactants | 15-30 |
| Nonionic surfactants, soap | 5-15 |
| Phosphonate, Soap | <5 |
| Boric acid | ≤1 |
| Other ingredients: e.g. optical brighteners, perfumes, preservatives | |
| pH 8.2-8.6 | |

Figure 3A:
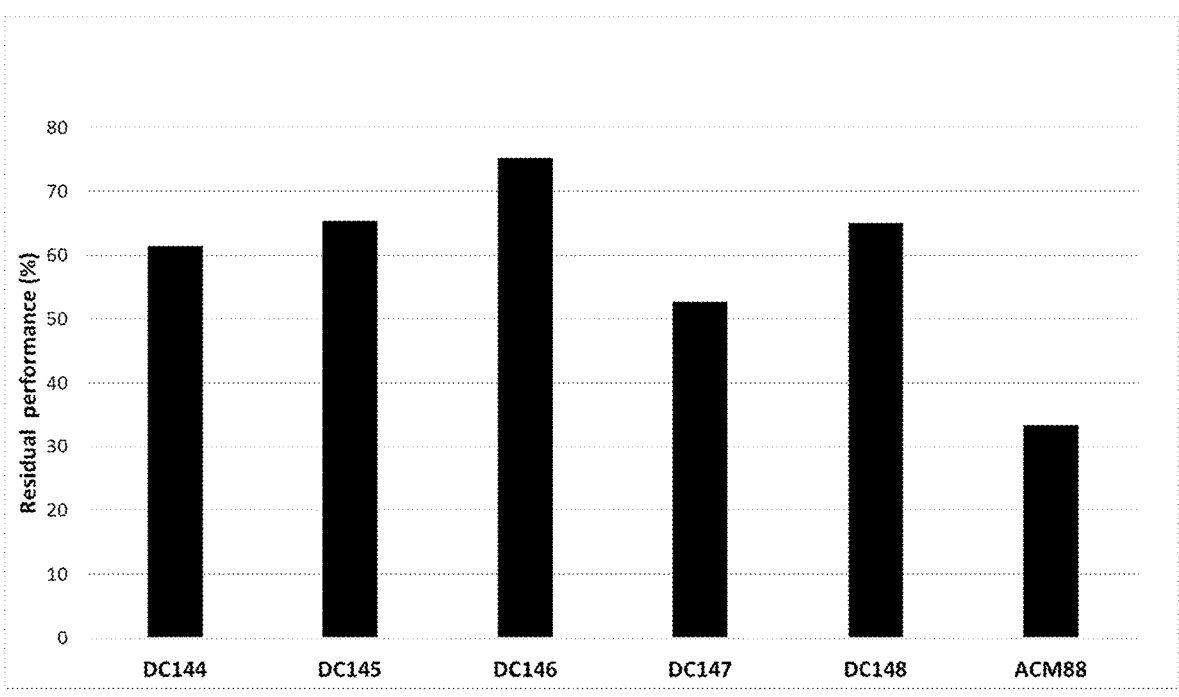
FIG. 3A shows the residual performance of variants DC144-DC148 compared to ACM88.
Figure 3B:
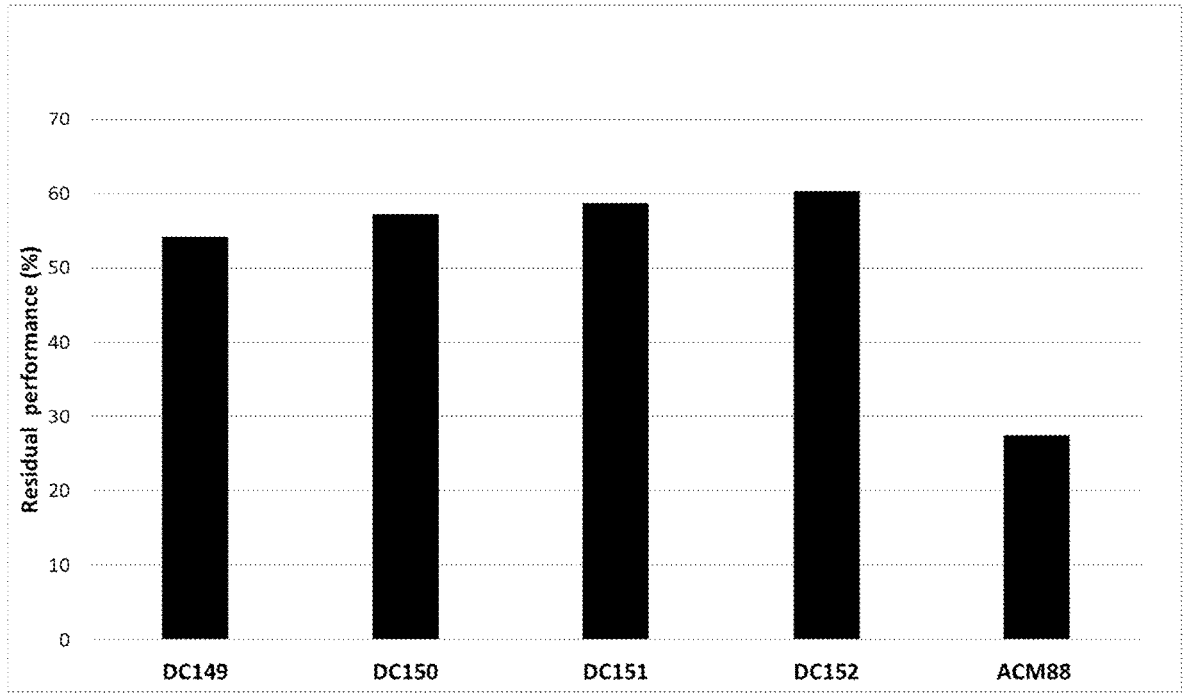
FIG. 3B shows the residual performance of variants DC149-DC152 compared to ACM88.

The increase of residual performance of variant was further calculated in relation to the residual performance obtained with ACM88.as shown in table 3. Results obtained with variants DC144-DC148 are shown in FIG. 3A and results with variants DC149-DC152 in FIG. 3B also as residual performance. All of these variants showed considerably better stability compared to ACM88 measured as color revival (depilling) performance. The best variants (DC146, DC150, DC151 and DC152) showed both improved performance (example 2) and at least two times higher stability (Table 3). compared to ACM88. DC150 comprising least substitutions already showed improved properties and the properties were further improved with the individual substitutions of the variants DC146, DC151 and DC152, showing even better stability measured as color revival performance.

Figure 4A:
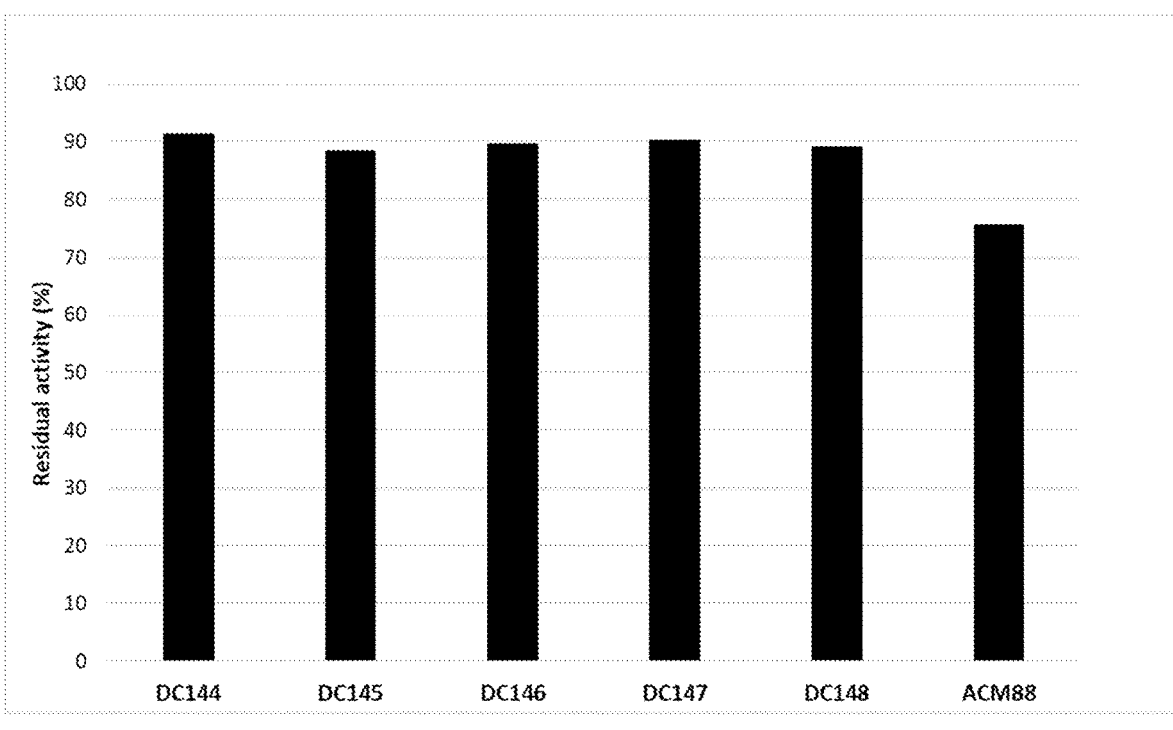
FIG. 4A shows the residual activity (%) of variants D144-D148 compared to ACM88.
Figure 4B:
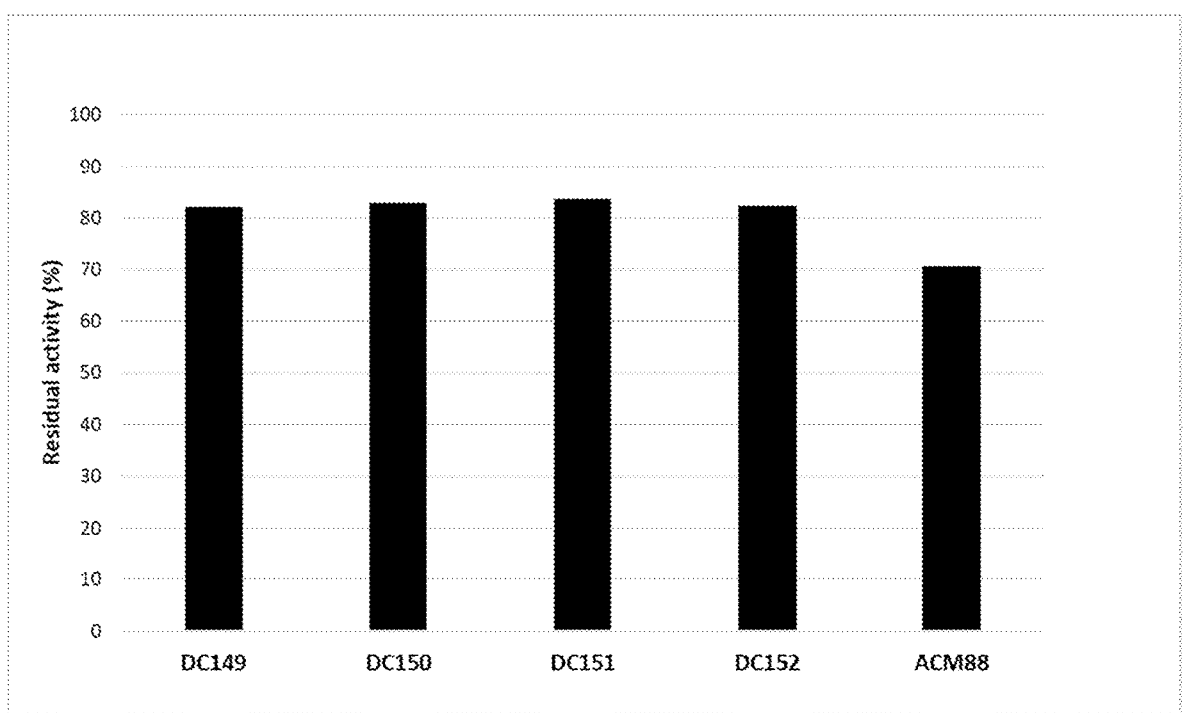
FIG. 4B shows the residual activity (%) of variants D149-D152 compared to ACM88.

The stability of variants was measured also by analyzing the NCU activity. Results were calculated as residual activity (%) which was obtained by dividing the activity of sample after storage by the initial activity of the sample. Results obtained with variants DC144-DC148 are shown in FIG. 4A and results with variants DC149-DC152 in FIG. 4B. The loss of performance was much greater than the loss of the analytical NCU-activity on CMC-substrate after storage in protease containing detergent. This was found to be mainly a result from loss of CBD which was detected by SDS-PAGE analysis (data not shown). Loss of CBD affects more on the performance than on the analytical activity, therefore the stability of variants measured with NCU activity assay showed smaller differences compared to ACM88. However, the stability of variants DC144-DC152 was increased compared to ACM88 also when measured as residual activity.

TABLE 3

The stability of color revival performance. Increase of residual performance of variant is given in relation to that of ACM88 after storage at 20-22° C. (3 or 4 d) in commercial liquid detergent containing protease (Savinase 16 L). Cellulases were initially added in detergent in such amount that dosages would be 2 or 3 activity units (NCU) per ml of wash solution

| Variant | Conditions | Stability increase (%) |
|---|---|---|
| DC121 | 3 NCU/ml, 3 d | 24 |
| DC133 | 3 NCU/ml, 3 d | 52 |
| DC139 | 3 NCU/ml, 3 d | 28 |

TABLE 3-continued

The stability of color revival performance. Increase of residual
performance of variant is given in relation to that of ACM88
after storage at 20-22° C. (3 or 4 d) in commercial liquid
detergent containing protease (Savinase 16 L). Cellulases were
initially added in detergent in such amount that dosages would
be 2 or 3 activity units (NCU) per ml of wash solution

| Variant | Conditions | Stability increase (%) |
|---------|-----------|------------------------|
| DC140 | 3 NCU/ml, 3 d | 22 |
| DC141 | 3 NCU/ml, 3 d | 51 |
| DC143 | 3 NCU/ml, 3 d | 41 |
| DC144 | 2 NCU/ml, 4 d | 84 |
| DC145 | 2 NCU/ml, 4 d | 96 |
| DC146 | 2 NCU/ml, 4 d | 126 |
| DC147 | 2 NCU/ml, 4 d | 58 |
| DC148 | 2 NCU/ml, 4 d | 95 |
| DC149 | 2 NCU/ml, 4 d | 98 |
| DC150 | 2 NCU/ml, 4 d | 109 |
| DC151 | 2 NCU/ml, 4 d | 114 |
| DC152 | 2 NCU/ml, 4 d | 120 |

Example 4. Long Term Stability of Selected
ACM88 Variants in Detergents at 30° C. Measured
as Color Revival Performance Enzyme preparations with similar activity levels were prepared from bioreactor cultivation samples of variants DC144, DC145, DC146, DC150 and reference ACM88 produced as described in Example 1. The stability of color revival (performance) was tested by washing tests similar to that described in Example 2.

Cellulases were initially added in detergent in such amount that dosages would be 2 units (NCU) per ml of wash liquor. DC146 was compared to ACM88 in 3 different detergents: detergent concentrates 1 and 2 containing a commercial protease and Commercial liquid base detergent in which 0.7% w/w of prestabilized protease Savinase Ultra 16L (Novozymes) was added. In addition to that, variants DC144, DC145, DC146 and DC150 were tested against ACM88 in a commercial detergent concentrate 3 containing a different commercial protease than in other detergents. Samples in plastic tubes with caps were incubated at 30° C. for several days or weeks depending on the test. The performance of stored samples was compared to washes, in which the cellulases had been added fresh into washing liquor containing detergent and protease. Results were calculated as residual performance (%), as described in Example 3.

Figure 5:
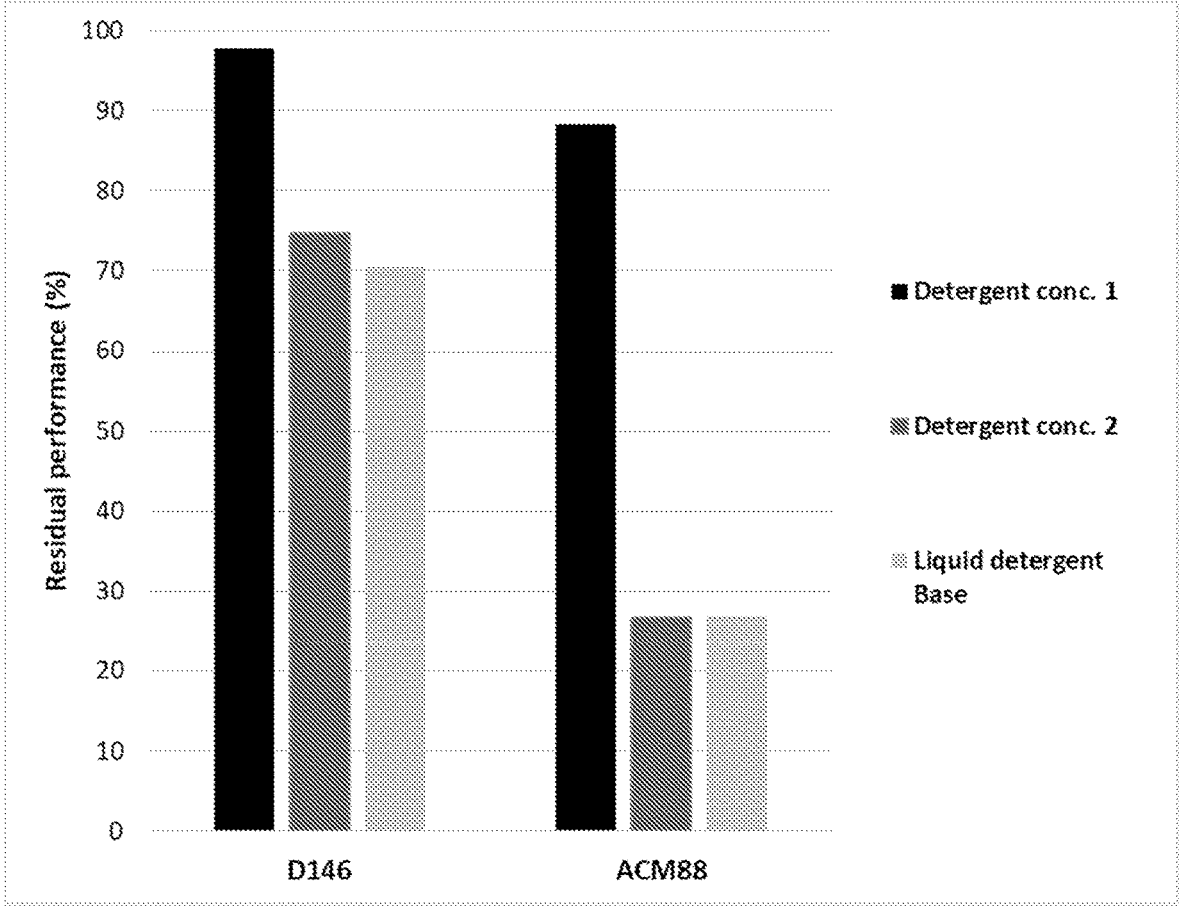
FIG. 5 shows the residual performance of DC146 and ACM88 as color revival (depilling) effect after storage (30° C., 9 d) in three different detergent formulations: Liquid detergent concentrates 1 and 2 containing a commercial protease and Liquid detergent base in which 0.7% w/w Savinase Ultra 16 L had been added.
Figure 6:
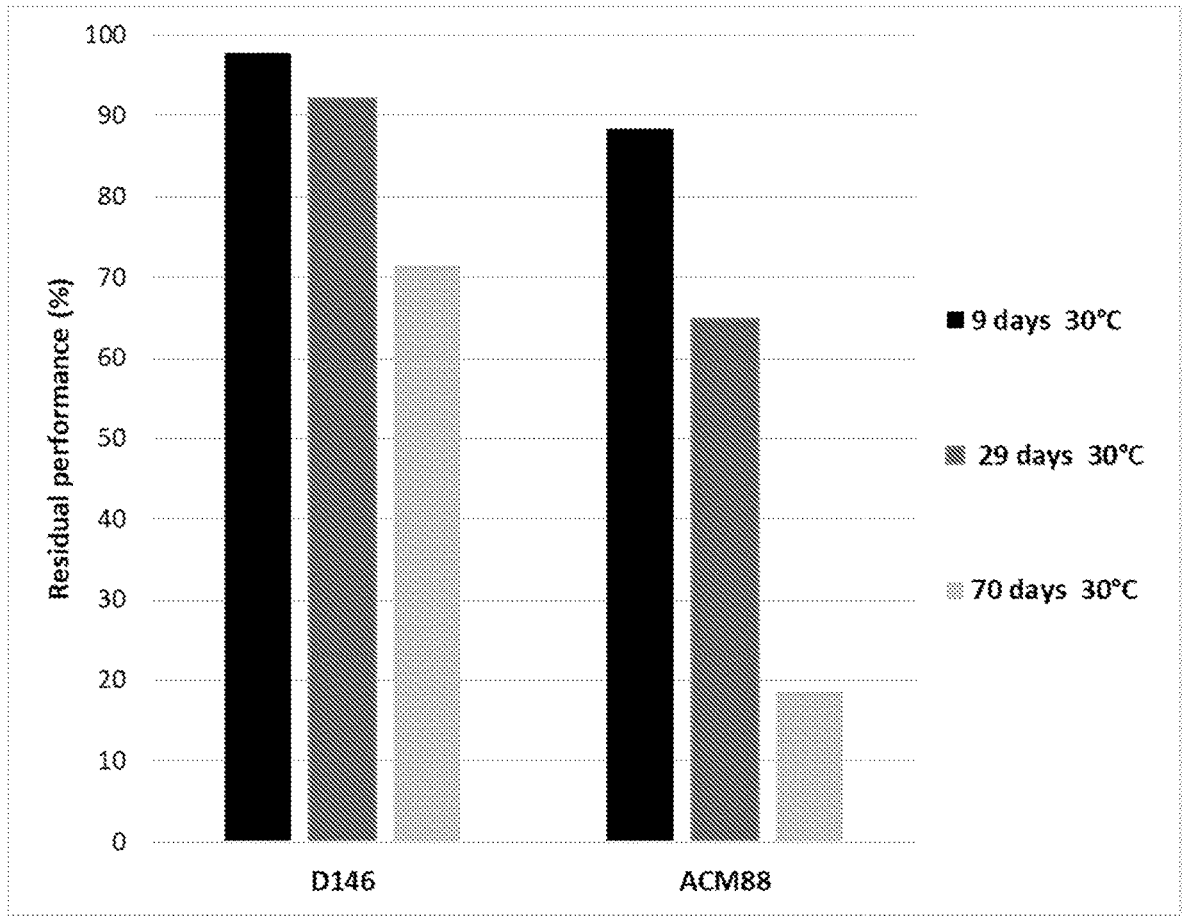
FIG. 6 shows the residual performance of DC146 and ACM88 as color revival (depilling) effect during long term (over 10 weeks) storage at 30° C. in Liquid detergent concentrate 1 containing commercial protease.
Figure 7:
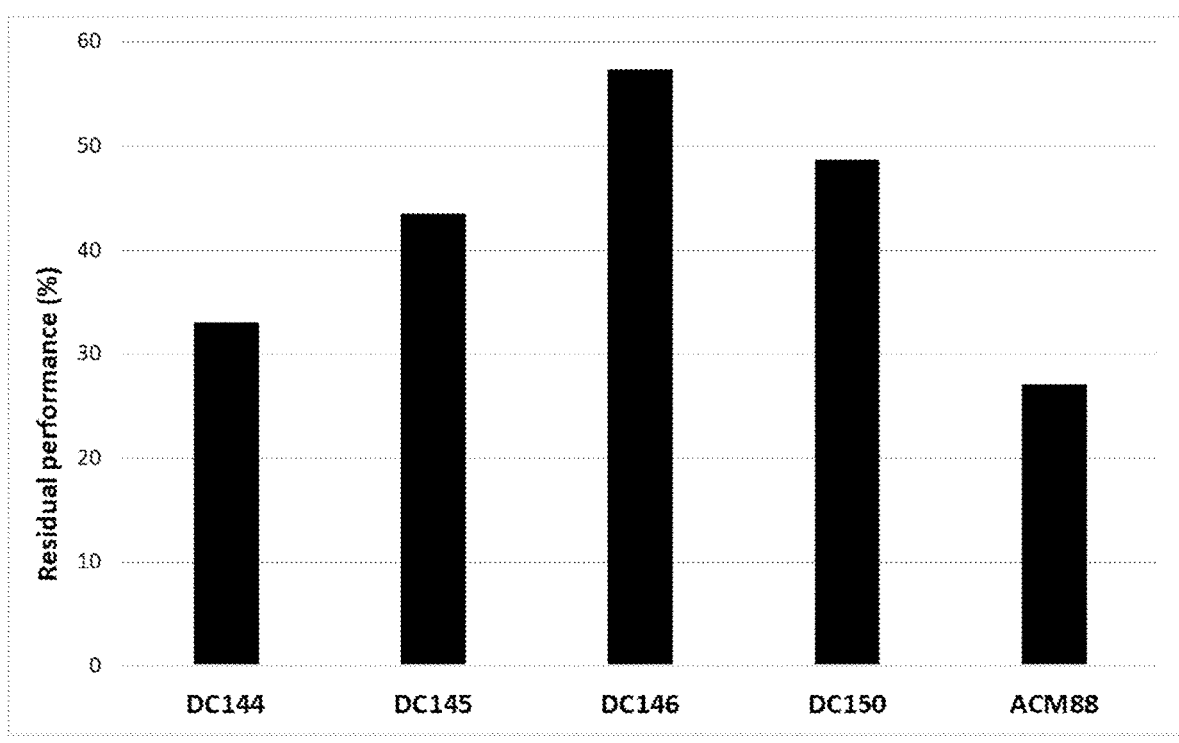
FIG. 7 shows the residual performance of variants DC144, DC145, DC146 and DC150 and ACM88 as color revival (depilling) effect after storage (30° C., 11 d) in Commercial liquid detergent concentrate 3 containing protease.

Based on results shown in FIG. 5, variant DC146 showed considerably better stability compared to ACM88 measured as color revival (depilling) effect after 9 days at 30° C. in all detergents tested. With detergent concentrate 1, the tests were carried out for several weeks. FIG. 6 shows that variant DC146 was efficient in protease containing detergent formulation even after 10 weeks storage at elevated temperature like 30° C. FIG. 7 shows that the stability of color revival effect compared to ACM88 was considerably improved with all variants DC144, DC145, DC146 and DC150 in a Commercial detergent concentrate 3 containing protease after storage (30° C., 11 d). Best results were obtained with DC146.

Example 5. Testing the Antigreying Performance of
Selected ACM88 Variants in Launder-Ometer Enzyme preparations with similar activity levels, prepared from bioreactor cultivation samples of variants DC145 and DC146 and the reference ACM88, were tested for anti-greying performance by a single wash method (40° C., 60 min, 16° dH) using carbon black (approx. 0.15 g/l) in a wash solution in addition to detergent (4.4 g/l).

Cotton interlock double jersey with optical brighteners (CN-42) sup-plied from CFT (Center for Testmaterials NV, the Netherlands) was used as test fabric. The fabric was first prewashed in a washing machine (15 min 50° C. and 60 min at 60° C.) and tumble dried, then cut to swatches of approx. 14-14.5 cm (total weight of 4 swatches 25 g).

As a source of carbon black RD-liq 01 from CFT containing 7 g of carbon black liquid (about 33% carbon black) in plastic bottles, that are normally intended for full scale washes in washing machine (one bottle per one single wash with test fabrics), were used. In this Example the method was adapted to small scale using approximately similar ratio of carbon black and water that would be in full scale. First a stock solution carbon black was prepared by placing an opened bottle of RD-liq 01 (i.e. about 2.3 g carbon black) in a decanter flask containing 1 liter of deionized water. The solution was stirred with a magnetic stirrer for overnight until the contents of the bottle were totally released. After that 65 g of stock solution mixed with 935 ml of synthetic tap water with hardness of 17.1° dH ending up to diluted carbon black solution having hardness of 16° dH and carbon black content approximately 0.15 g/l (or 0.45 g RD-liq 01).

For synthetic tap water with hardness of 17.1° dH the following stock solutions were prepared in deionized water (Milli-Q or equivalent):

Stock solution with 1000° d Calcium-hardness: $CaCl_2$× $2H_2O$ (1.02382.1000, Merck KGaA, Germany) 26.22 g/l Stock solution with 200° d Magnesium-hardness: $MgSO_4$×7 $H_2O$ (1.05886.1000, Merck KGaA, Germany) 8.79 g/l $H_2O$ $NaHCO_3$ stock solution: $NaHCO_3$ (1.06329.1000 Merck KGaA, Germany) 29.6 g/l.

14.2 ml $CaCl_2$) solution, 14.2 ml $MgSO_4$ solution and 10.0 ml of freshly made $NaHCO_3$ solution were added in volumetric flask in the given order, made up to 1 liter with deionized water and mixed. The hardness of water was determined by complexometric titration and found correct.

Antigreying tests were performed in Atlas LP-2 Launder-Ometer as follows. Launder-Ometer was first preheated to 40° C. 60 g of steel balls (diameter 0.6 cm), 1.1 g of commercial liquid detergent described in Table 2 in Example 3, 250 ml of diluted carbon black liquor and diluted enzyme (<1.0 ml) were added into 1.2 liter containers. After that, 4 swatches of prewashed test fabric CN-42 were added and the Launder-Ometer was run at 40° C. for 60 min with a rotation speed of 42 rpm. Enzymes were dosed 0.05, 0.1 and 0.2 activity units (NCU) per liter. Control sample contained no enzyme. Activity was measured as described in Example 1.

After the cellulase treatment in Launder-Ometer, the swatches were first quickly rinsed separately under running tap water (ca. 20° C.) to remove the steel balls, then rinsed separately under running water in specific cups containing holes for 3 times and finally dipped in a bucket containing water. After that the swatches were extracted in a washing machine and let to dry on a grid at room temperature. Enzyme treated fabrics and controls without enzyme were rinsed and extracted separately to avoid contamination.

Antigreying performance of cellulase was evaluated by measuring reflectance of test fabrics by Konica Minolta CM3610A spectrophotometer as Y-value (illuminant D65/ 10°, 420 nm cut). Antigreying performance was calculated as ΔY (delta Y), which means value Y of enzyme treated fabric minus value Y of fabric treated with carbon black and detergent containing washing liquor without enzyme (enzyme blank, control). Values were the average of 4 swatches. The higher the Y or ΔY value, the better the antigreying effect and whiteness of the fabric.

Figure 8:
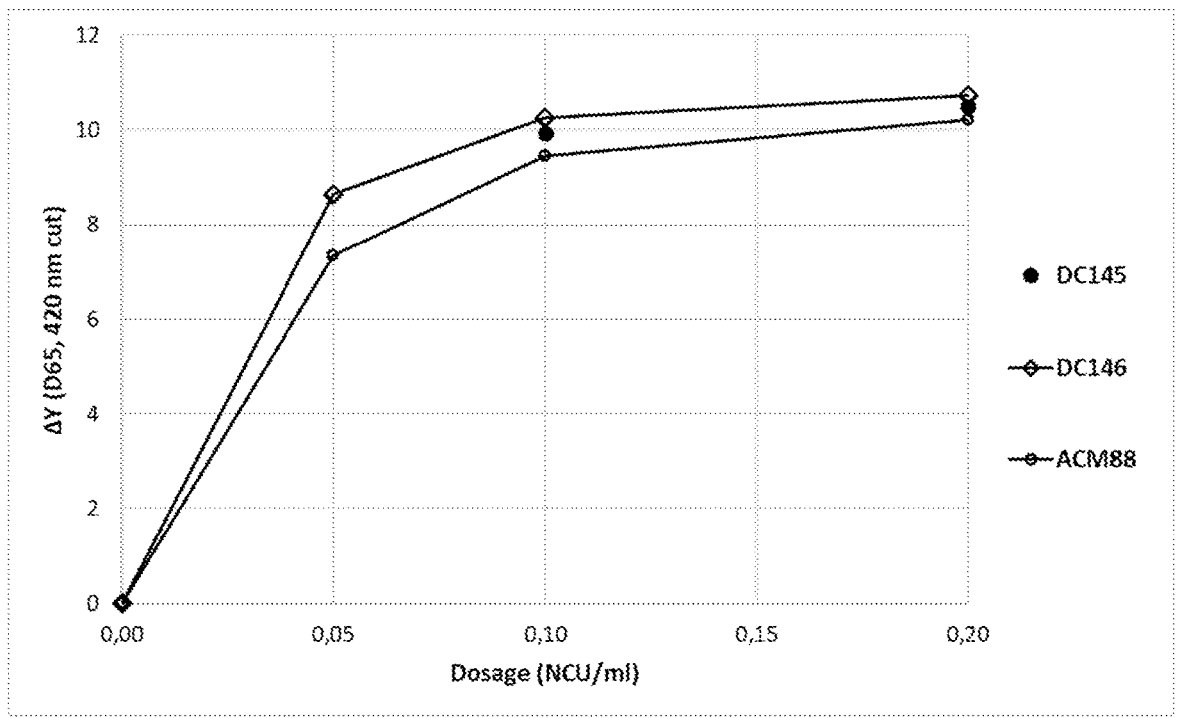
FIG. 8 shows the antigreying performance of variants DC145 and DC146 and ACM88 in a single wash in the presence of carbon black in a commercial liquid detergent. Washing conditions: 40° C., 60 min, 16° dH, carbon black approx. 0.15 g/l, detergent 4.4 g/l, enzyme dosage 0-0,2 NCU/ml.

Results in FIG. 8 show that variants DC145 and DC146 have excellent antigreying properties, at least as good as the reference ACM88 in liquid detergent.

Different non-binding example aspects and embodiments of the present invention have been illustrated in the foregoing. The embodiments are used merely to explain selected aspects or steps that may be utilized when implementing the present invention. Some embodiments may be presented herein only with a reference to a certain aspect of the invention. It should be appreciated that the embodiments may apply to other aspects of the present invention, as well. Consequently, any appropriate combination of the embodiments and the aspects may be formed. Any combination of aspects or embodiments as disclosed herein may also be made without at least one non-essential feature disclosed in an aspect or embodiment.

In an embodiment at least one component of a product of the present invention has a different structural or functional characteristic compared to the naturally occurring counterpart. In an embodiment the at least one component has a different structural or physical characteristic compared to the corresponding natural component from which the at least one component is derived from.

REFERENCES

Bailey M and Nevalainen H. 1981. Induction, isolation and testing of stable *Trichoderma reesei* mutants with improved production of solubilizing cellulase. Enzyme Microb. Technol. 3:153-157.

Gellissen G. (ed.). 2005. Production of recombinant proteins. Novel microbial and eukaryotic expression systems. Wiley-VCH Verlag Gmbh & Co. Weinheim, Germany.

Haakana H, Miettinen-Oinonen A, Joutsjoki V, Mäntylä A, Suominen P and Vehmaanpers J. 2004. Cloning of cellulase genes from *Melanocarpus albomyces* and their efficient expression in *Trichoderma reesei*. Enzyme Microb. Technol. 34:159-167.

Henrissat B. 1991. A classification of glycosyl hydrolases based on amino acid sequence similarities. Biochem. J. 280: 309-316.

Henrissat B. and Bairoch A. 1993. New families in the classification of glycosyl hydrolases based on amino acid sequence similarities. Bio-chem. J. 293: 781-788.

Henrissat B. and Bairoch A. 1996. Updating the sequence-based classification of glycosyl hydrolases. Biochem. J. 316: 695-696.

Joutsjoki VV, TK Torkkeli and KMH Nevalainen. 1993. Transformation of *Trichoderma reesei* with the Hormoconis resinae glucoamylase P (gamP) gene: production of a heterologous glucoamylase by *Trichoderma reesei*. Curr. Genet. 24:223-228.

Karhunen T, A Mäntylä, KMH Nevalainen and P L Suominen. 1993. High frequency one-step gene replacement in *Trichoderma reesei*. I. Endoglucanase I overproduction. Mol. Gen. Genet. 241:515-522.

Paloheimo M, A Mäntylä, J Kallio, and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttils M, H Nevalainen, M Rättö, E Salminen and J Knowles. 1987. A versatile transformation system for the cellulolytic filamentous fungus *Trichoderma reesei*. Gene 61:155-164.

Sambrook J and Russell DW. 2001. Molecular cloning, a laboratory manual. Cold Spring Harbor Laboratory, New York, US.

The invention claimed is:

1. A variant of a GH45 cellulase polypeptide, wherein the variant comprises a substitution Q167Y and substitutions in amino acid positions 210, 215, 220 and 225, wherein the amino acid positions are numbered with reference to a parent GH45 cellulase having an amino acid sequence set forth in SEQ ID NO: 1; wherein the variant has at least 95% sequence identity with the parent GH45 cellulase of SEQ ID NO: 1; and wherein the variant has improved protease stability in comparison to the parent GH45 cellulase as determined a after storage for three days at 20-22° C. in a liquid detergent comprising 0.7% (w/w) protease.

2. The variant of claim 1, wherein the substitutions comprise the substitutions N210S, N215R/S, N220S and N225S.

3. The variant of claim 1, wherein the variant further comprises one or more further substitutions in the positions 23, 44, 65, 66, 77, 193, 219, 242 and 244.

4. The variant of claim 3, wherein the further substitution is one or more of the substitutions S23P, K44N, D65E, N66Q, A77S, T193V, G219S, S242G and G244T.

5. The variant of claim 3, comprising the following substitutions: S23P, D65E, N66Q, A77S, N210S, N215R, G219S, N220S, N225S, and G244T.

6. An isolated nucleic acid molecule comprising a nucleotide sequence which encodes the variant of claim 1.

7. A recombinant expression vector comprising the nucleotide sequence of claim 6 operably linked to regulatory sequences capable of directing expression of the gene encoding said variant cellulase in a suitable host.

8. A host cell comprising the recombinant expression vector according to claim 7, the host cell being selected from the group consisting of: fungal cells, bacterial cells, gram-positive Bacilli, gram negative bacteria, actinomycetales, and yeasts.

9. A method of producing a variant of a GH45 cellulase polypeptide, wherein the variant comprises a substitution 0167Y and substitutions in amino acid positions 210, 215, 220 and 225, wherein the amino acid positions are numbered with reference to a parent GH45 cellulase having an amino acid sequence set forth in SEQ ID NO: 1; wherein the variant has at least 95% sequence identity with the parent GH45 cellulase of SEQ ID NO: 1; and wherein the variant has improved protease stability in comparison to the parent GH45 cellulase as determined after storage for three days at 20-22° C. in a liquid detergent comprising 0.7% a (w/w) protease; said method comprising culturing the host cell of claim 8.

10. A method of producing an enzyme composition comprising the steps of culturing the host cell of claim 8 and either recovering the variant from the cells, or separating the cells from the culture medium and recovering the whole culture broth comprising the variant.

11. An enzyme composition comprising the variant of claim 1 and at least one:
- polyol selected from propylene glycol, glycerol, a sugar, sugar alcohol, sorbitol, hexylene glycol;
- preservative selected from organic acids, sodium benzoate, hydroxybenzoate, benzisothiazolinone (BIT) or a combination thereof,
- formic acid, lactic acid, boric acid, boric acid derivative, aromatic borate ester, phenyl boronic acid derivative, peptide, reversible subtilisin inhibitors or a combination thereof;
- enzyme selected from proteases, amylases, cellulases, lipases, xylanases, mannanases, cutinases, esterases, phytases, nucleases, pectinases, pectinolytic enzymes, pectate lyases, carbohydrases, arabinases, galactanases, xanthanases, xyloglucanase, laccases, peroxidases and oxidases with or without a mediator, or a combination thereof,
- salt selected from sodium chloride, potassium chloride, potassium (hydrogen)phosphate, sodium (hydrogen) phosphate, ammonium sulfate, potassium sulfate, or a combination thereof, and/or filler or carrier selected from maltodextrin, flour, sodium chloride, sulfate, sodium sulfate, sodium acid pyrophosphate, tetrasodium pyrophosphate, polyethylene glycol, or a combination thereof.

12. The enzyme composition of claim 11, characterized in that said enzyme composition is in the form of a solution, dispersion, paste, powder, pellet, granule, granulate, coated granulate, tablet, cake, crystal, crystal slurry or gel.

13. A detergent composition comprising a detergent and the variant of claim 1.

14. The detergent composition of claim 13, in the form of a bar, a homogenous tablet, a tablet having two or more layers, a pouch having one or more compartments, a regular powder, a compact powder, a granule, a paste, a gel, a regular liquid, a compact liquid, or a concentrated liquid.

15. The detergent composition of claim 13, characterized in that said composition comprises one or more additional enzymes selected from the group of proteases, amylases, cellulases, lipases, xylanases, mannanases, cutinases, esterases, nucleases, pectinases, pectate lyases, pectinolytic enzymes, carbohydrases, arabinases, galactanases, xanthanases, xyloglucanases, laccases, peroxidases and oxidases, and wherein the detergent composition comprises one or more of surfactants, builders, chelators, chelating agents, bleach system, bleach components, polymers, fabric conditioners, foam boosters, suds suppressors, dyes, perfume, tannish inhibitors, optical brighteners, bactericides, fungicides, soil suspending agents, anticorrosion agents, hydrotropes, fabric hueing agents, dispersants, dye transfer inhibiting agents, fluorescent whitening agents, soil release polymers, anti-redepositions agents, anti-shrink agents, anti-wrinkling agents, bactericides, binders, carriers, dyes, enzyme stabilizers, fabric softeners, fillers, foam regulators, perfumes, pigments, buffers, preservatives, sod suppressors, solvents, structurants for liquid detergents, structure elasticizing agents, enzyme inhibitors, stabilizers, enzyme activators, transferase(s), hydrolytic enzymes, oxido reductases, bluing agents, fluorescent dyes, antioxidants, and solubilizers.

16. A method for treating cellulosic material, wherein the method comprises reacting the cellulosic material with the variant of claim 1.

17. The method of claim 16, wherein the cellulosic material is textile material, plants used in animal feed, or wood-derived pulp or secondary fiber.

18. A method for treating a textile material, wherein the method comprises contacting the textile material with a detergent composition comprising a detergent and a variant of a GH45 cellulase polypeptide, wherein the variant comprises a substitution Q167Y and substitutions in amino acid positions 210, 215, 220 and 225, wherein the amino acid positions are numbered with reference to a parent GH45 cellulase having an amino acid sequence set forth in SEQ ID NO: 1; wherein the variant has at least 95% sequence identity with the parent GH45 cellulase of SEQ ID NO: 1; and wherein the variant has improved protease stability in comparison to the parent GH45 cellulase as determined after storage for three days at 20-22° C. in a liquid detergent comprising 0.7% (w/w) protease.

19. A method for antigreying, stain removal, fiber and color care, biostoning or biofinishing which comprises a step of adding the variant of claim 1 to liquid used in treating fabric containing cellulose or a cellulose derivative, a garment, or other textile material.

20. The method of claim 19, wherein the textile materials are manufactured of natural cellulose containing fibers or manmade cellulose containing fibers or are mixtures thereof.

21. A method of modifying, degrading, and/or removing cellulose in biomass, wherein the method comprises treating said biomass with the variant of claim 1.

22. A detergent composition comprising a detergent and the enzyme composition of claim 11.

23. A method for treating cellulosic material, wherein the method comprises reacting the cellulosic material with the enzyme composition of claim 11.

24. A method for antigreying, stain removal, fiber and color care, biostoning or biofinishing which comprises a step of adding the enzyme composition of claim 11 to liquid used in treating fabric containing cellulose or a cellulose derivative, a garment, or other textile material.

25. A method of manufacturing food or feed containing cellulosic material, wherein the method comprises reacting the cellulosic material with the enzyme composition of claim 11.

26. The host cell of claim 8, wherein the host cell is *Trichoderma reesei.*

27. The host cell of claim 8, wherein the host cell is a filamentous fungal cell.

28. The host cell of claim 27, wherein the filamentous fungal cell is selected from fungal cells belonging to Genera *Trichoderma* (anamorph of *Hypocrea*), *Fusarium, Gibberella, Nectria, Stachybotrys, Claviceps, Metarhizium, Villosiclava, Ophiocordyceps, Cephalosporium,* or *Scedosporium*.

29. The host cell of claim 27, wherein the fungal cell is selected from *Trichoderma reesei* (*Hypocrea jecorina*), *T. citrinoviridae, T. longibrachiatum, T. virens, T. harzianum, T. asperellum, T. atroviridae, T. parareesei, Fusarium oxysporum, F. gramineanum, F. pseudograminearum, F. venenatum, Gibberella fujikuroi, G. monilformis, G. zeaea, Nectria, haematococca, Stachybotrys chartarum, S. chlorohalonata, Claviceps purpurea, Metarhizium acridum, M. anisophiae, Villosiclava virens, Ophiocordyceps sinensis, Acremonium chrysogenum,* and *Scedosporium apiospermum, Aspergillus niger, Aspergillus awamori, Aspergillus oryzae, Chrysosporium lucknowense, Mycehiophthora thermophila, Humicola insolens,* and *Humicola grisea*.

*     *     *     *     *

SEQUENCE LISTING

<160> NUMBER OF SEQ ID NOS: 3

<210> SEQ ID NO 1
<211> LENGTH: 281
<212> TYPE: PRT
<213> ORGANISM: Acremonium thermophilum

<400> SEQUENCE: 1

```
Leu Asp Gly Lys Ser Thr Arg Tyr Trp Asp Cys Cys Lys Pro Ser Cys
1               5                   10                  15

Gly Trp Ala Gly Lys Ala Ser Val Asn Gln Pro Val Phe Ser Cys Ser
            20                  25                  30

Ala Asp Trp Gln Arg Ile Ser Asp Phe Asn Ala Lys Ser Gly Cys Asp
        35                  40                  45

Gly Gly Asn Ala Tyr Ser Cys Ala Asp Gln Thr Pro Trp Ala Val Asn
    50                  55                  60

Asp Asn Phe Ser Tyr Gly Phe Ala Ala Thr Ala Ile Ala Gly Gly Ser
65                  70                  75                  80

Glu Gln Ser Trp Cys Cys Ala Cys Tyr Ala Leu Thr Phe Asn Ser Gly
                85                  90                  95

Pro Val Ala Gly Lys Thr Met Val Val Gln Ser Thr Ser Thr Gly Gly
            100                 105                 110

Asp Leu Gly Glu Asn His Phe Asp Leu Ala Ile Pro Gly Gly Gly Val
        115                 120                 125
```

```
Gly Ile Phe Asn Gly Cys Gln Ser Gln Phe Gly Gly Leu Pro Gly Ala
    130                 135                 140

Gln Tyr Gly Gly Ile Gln Asp Arg Ser Gln Cys Ser Ser Phe Pro Ala
145                 150                 155                 160

Pro Leu Gln Pro Gly Cys Gln Trp Arg Phe Asp Trp Phe Gln Asn Ala
                165                 170                 175

Asp Asn Pro Thr Phe Thr Phe Gln Arg Val Gln Cys Pro Ser Glu Leu
                180                 185                 190

Thr Ser Arg Thr Gly Cys Lys Arg Asp Asp Asp Ala Asn Tyr Pro Val
                195                 200                 205

Phe Asn Pro Pro Ser Gly Asn Pro Ser Gly Gly Asn Pro Pro Gly Gly
    210                 215                 220

Asn Pro Pro Gly Thr Thr Thr Thr Arg Arg Pro Ala Thr Thr Thr Gly
225                 230                 235                 240

Ser Ser Pro Gly Pro Thr Gln Ser His Tyr Gly Gln Cys Gly Gly Ile
                245                 250                 255

Gly Tyr Ser Gly Pro Thr Val Cys Ala Ser Gly Thr Thr Cys Gln Val
                260                 265                 270

Leu Asn Pro Tyr Tyr Ser Gln Cys Leu
    275                 280
```

```
<210> SEQ ID NO 2
<211> LENGTH: 298
<212> TYPE: PRT
<213> ORGANISM: Acremonium thermophilum

<400> SEQUENCE: 2

Met Tyr Arg Lys Leu Ala Val Ile Ser Ala Phe Leu Ala Thr Ala Arg
1               5                   10                  15

Ala Leu Asp Gly Lys Ser Thr Arg Tyr Trp Asp Cys Cys Lys Pro Ser
                20                  25                  30

Cys Gly Trp Ala Gly Lys Ala Ser Val Asn Gln Pro Val Phe Ser Cys
                35                  40                  45

Ser Ala Asp Trp Gln Arg Ile Ser Asp Phe Asn Ala Lys Ser Gly Cys
    50                  55                  60

Asp Gly Gly Asn Ala Tyr Ser Cys Ala Asp Gln Thr Pro Trp Ala Val
65                  70                  75                  80

Asn Asp Asn Phe Ser Tyr Gly Phe Ala Ala Thr Ala Ile Ala Gly Gly
                85                  90                  95

Ser Glu Gln Ser Trp Cys Cys Ala Cys Tyr Ala Leu Thr Phe Asn Ser
                100                 105                 110

Gly Pro Val Ala Gly Lys Thr Met Val Val Gln Ser Thr Ser Thr Gly
                115                 120                 125

Gly Asp Leu Gly Glu Asn His Phe Asp Leu Ala Ile Pro Gly Gly Gly
    130                 135                 140

Val Gly Ile Phe Asn Gly Cys Gln Ser Gln Phe Gly Gly Leu Pro Gly
145                 150                 155                 160

Ala Gln Tyr Gly Gly Ile Gln Asp Arg Ser Gln Cys Ser Ser Phe Pro
                165                 170                 175

Ala Pro Leu Gln Pro Gly Cys Gln Trp Arg Phe Asp Trp Phe Gln Asn
                180                 185                 190

Ala Asp Asn Pro Thr Phe Thr Phe Gln Arg Val Gln Cys Pro Ser Glu
                195                 200                 205

Leu Thr Ser Arg Thr Gly Cys Lys Arg Asp Asp Asp Ala Asn Tyr Pro
```

-continued

```
        210                 215                 220

Val Phe Asn Pro Pro Ser Gly Asn Pro Ser Gly Gly Asn Pro Pro Gly
225                 230                 235                 240

Gly Asn Pro Pro Gly Thr Thr Thr Thr Arg Arg Pro Ala Thr Thr Thr
                245                 250                 255

Gly Ser Ser Pro Gly Pro Thr Gln Ser His Tyr Gly Gln Cys Gly Gly
            260                 265                 270

Ile Gly Tyr Ser Gly Pro Thr Val Cys Ala Ser Gly Thr Thr Cys Gln
            275                 280                 285

Val Leu Asn Pro Tyr Tyr Ser Gln Cys Leu
        290                 295

<210> SEQ ID NO 3
<211> LENGTH: 1079
<212> TYPE: DNA
<213> ORGANISM: Acremonium thermophilum

<400> SEQUENCE: 3
atgtatcgga agttggccgt catctcggcc ttcttggcca cagctcgtgc cctcgacgga      60
aagtcgacga ggtatgccaa tcctcgtacc tctgccctct gtagaaacaa gtgaccgact     120
gcaaagacag atactgggac tgctgcaagc cgtcctgcgg ctgggccgga aaggcctcgg     180
tgaaccagcc cgtcttctcg tgctcggccg actggcagcg catcagcgac ttcaacgcga     240
agtcgggctg cgacggaggc aacgcctact cgtgcgccga ccagacgccc tgggcggtca     300
acgacaactt ctcgtacggc ttcgcagcca cggccatcgc cggcggctcc gagcagagct     360
ggtgctgcgc ctgctatgcg tgagttctct gcaagccgct tcccacccccc gctttctgtg     420 caggccgctt cccccctacc cacccacttc cccccccccg cctctgtgat cgggcatccg     480
agctaagttg cgtgtcgtcc agactcacct tcaactcggg ccccgtcgcg ggcaagacca     540
tggtggtgca gtcgaccagc accggcggcg acctgggcga gaaccacttc gacctcgcca     600 tcccccggcgg cggcgtgggc atcttcaacg gctgccagtc ccagttcggc ggcctccccg     660
gcgcccagta cggcggcatc caggaccgca gccagtgctc gtccttcccc gcgccgctcc     720
agccgggctg ccagtggcgc ttcgactggt tccagaacgc cgacaacccc accttcacct     780
tccagcgcgt gcagtgcccg tccgagctca cgtcccgcac gggctgtaag cgcgacgacg     840
acgccaacta tcccgtcttc aacccgcctt cgggcaaccc tagcggcggc aaccctcccg     900
gcggaaaccc gcctggcacc accaccaccc gccgcccagc cactaccact ggaagctctc     960
ccggacctac ccagtctcac tacggccagt gcggcggtat tggctacagc ggccccacgg    1020
tctgcgccag cggcacaact tgccaggtcc tgaacccttta ctactctcag tgcctgtaa     1079
```